United States Patent
Babu et al.

(10) Patent No.: US 12,288,621 B2
(45) Date of Patent: Apr. 29, 2025

(54) APPARATUS AND A METHOD FOR GENERATING A DIAGNOSTIC LABEL

(71) Applicant: Anumana, Inc., Cambridge, MA (US)

(72) Inventors: Melwin Babu, Kerala (IN); Sravan Kumar Lalam, Karnataka (IN); Rakesh Barve, Bengaluru (IN); Kirnesh Nandan, Karnataka (IN); Hari Krishna Kunderu, Hyderabad (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/230,043

(22) Filed: Aug. 3, 2023

(65) Prior Publication Data

US 2025/0046447 A1    Feb. 6, 2025

(51) Int. Cl.
    *G16H 50/20* (2018.01)
    *G16H 10/60* (2018.01)
    *G16H 15/00* (2018.01)
    *G16H 70/60* (2018.01)

(52) U.S. Cl.
    CPC ............. *G16H 50/20* (2018.01); *G16H 10/60* (2018.01); *G16H 15/00* (2018.01); *G16H 70/60* (2018.01)

(58) Field of Classification Search
    CPC .............................................. G06Q 50/20–26
    See application file for complete search history.

(56) References Cited

U.S. PATENT DOCUMENTS

| 8,199,997 B2 | 6/2012 | Rutenberg et al. |
| 11,449,973 B2 | 9/2022 | Rutenberg et al. |
| 11,977,952 B1 * | 5/2024 | Golchha ............... G06K 7/1413 |
| 11,983,494 B1 * | 5/2024 | Watkins ................ G06F 40/279 |
| 11,997,240 B1 * | 5/2024 | Perugupalli .......... H04N 1/3876 |

(Continued)

FOREIGN PATENT DOCUMENTS

CN    113241135 A    8/2021

OTHER PUBLICATIONS

Raghu Aniruddh et al: "Contrastive Pre-Training for Multimodal Medical Time Series", Dec. 2, 2022 (Dec. 2, 2022), pp. 1-9, XP093234736, Retrieved from the Internet: URL:https://openreview.net/pdf?id=4M-D9j9g FHW [retrieved on Dec. 16, 2024].

(Continued)

*Primary Examiner* — Neal Sereboff
(74) *Attorney, Agent, or Firm* — Caldwell Intellectual Property Law

(57) ABSTRACT

An apparatus for generating a diagnostic label is disclosed. The apparatus includes at least a processor and memory communicatively connected to the at least a processor. The memory instructs the processor to receive a plurality of electrocardiogram signals and a plurality of electronic health records from a user. The memory instructs the processor to generate a plurality of structured electronic health records using the plurality of electronic health records. The memory instructs the processor to generate a plurality of representations as a function of the plurality of electrocardiogram signals and the plurality of structured electronic health records using a representation machine learning model. The memory instructs the processor to generate a diagnostic label as a function of the plurality of representations. The memory instructs the processor to display the diagnostic label using a display device.

16 Claims, 15 Drawing Sheets

(56) References Cited

U.S. PATENT DOCUMENTS

| | | | | |
|---|---|---|---|---|
| 2020/0303072 | A1* | 9/2020 | Drokin | G16H 10/60 |
| 2021/0043326 | A1* | 2/2021 | Janssen | G16H 40/63 |
| 2022/0058776 | A1 | 2/2022 | Ozcan et al. | |
| 2022/0384045 | A1* | 12/2022 | Zimmerman | A61B 5/7275 |
| 2024/0046109 | A1* | 2/2024 | Anand | G06N 5/01 |
| 2024/0126794 | A1* | 4/2024 | Cook | H04L 51/02 |
| 2024/0143838 | A1* | 5/2024 | Ardhanari | G16H 30/40 |

OTHER PUBLICATIONS

Lalam Sravan Kumar et al: "ECG Representation Learning with Multi-Modal EHR Data", Transactions on Machine Learning Research, Nov. 30, 2023 (Nov. 30, 2023), pp. 1-24, XP093234530, Retrieved from the Internet: URL: https://openreview.net/pdf?id=UxmvCwuTMG [retrieved on Dec. 16, 2024].

European Search Report; EP 24 19 0463, By: Bonnet, Clara; Dec. 16, 2024.

* cited by examiner

APPARATUS AND A METHOD FOR GENERATING A DIAGNOSTIC LABEL

FIELD OF THE INVENTION

The present invention generally relates to the field of artificial intelligence. In particular, the present invention is directed to an apparatus and a method for generating a diagnostic label.

BACKGROUND

In modern healthcare settings, the collection and storage of patient health data have evolved significantly. Electronic health records (EHR) systems have been widely adopted to organize structured patient data, including demographic information, diagnoses, medications, and laboratory results. However, effectively harnessing the wealth of information contained within EHRs, along with textual data such as physician notes, reports, and patient narratives, and correlating it with diagnostic ECG signals, remains a challenge.

SUMMARY OF THE DISCLOSURE

In an aspect, an apparatus for generating a diagnostic label is disclosed. The apparatus includes at least a processor and memory communicatively connected to the at least a processor. The memory instructs the processor to receive a plurality of electrocardiogram signals and a plurality of electronic health records from a user. The memory instructs the processor to generate a plurality of structured electronic health records using the plurality of electronic health records. The memory instructs the processor to generate a plurality of representations as a function of the plurality of electrocardiogram signals and the plurality of structured electronic health records using a representation machine learning model. Generating the plurality of representations includes training the representation machine learning model using representation training data, wherein the representation training data comprises a plurality of data entries containing the plurality of electrocardiogram signals and the structured electronic health records as inputs correlated to the plurality of representations as outputs. Generating the plurality of representations also includes generating the plurality of representations as a function of the plurality of electrocardiogram signals and the plurality of structured electronic health records using the trained representation machine learning model. The memory instructs the processor to generate a diagnostic label as a function of the plurality of representations. The memory instructs the processor to display the diagnostic label using a display device.

In another aspect, a method for generating a diagnostic label is disclosed. The method includes receiving, using at least a processor, a plurality of electrocardiogram signals from a user. The method includes receiving, using the at least a processor, a plurality of electronic health records from the user, wherein the plurality of electronic health records includes a plurality of metadata. The method includes generating, using the at least a processor, a plurality of structured electronic health records using the plurality of electronic health records. The method includes generating, using the at least a processor, a plurality of representations as a function of the plurality of electrocardiogram signals and the plurality of structured electronic health records using a representation machine learning model. Generating the plurality of representations includes training the representation machine learning model using representation training data, wherein the representation training data comprises a plurality of data entries containing the plurality of electrocardiogram signals and the structured electronic health records as inputs correlated to the plurality of representations as outputs. Generating the plurality of representations also includes generating the plurality of representations as a function of the plurality of electrocardiogram signals and the plurality of structured electronic health records using the trained representation machine learning model. The method includes generating, using the at least a processor, a diagnostic label as a function of the plurality of representations. The method includes displaying, using the at least a processor, the diagnostic label using a display device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and a method for generating a diagnostic label is disclosed. The apparatus includes at least a processor and memory communicatively connected to the at least a processor. The memory instructs the processor to receive a plurality of electrocardiogram signals and a plurality of electronic health records from a user. The memory instructs the processor to generate a plurality of structured electronic health records using the plurality of electronic health records. The memory instructs the processor to generate a plurality of representations as a function of the plurality of electrocardiogram signals and the plurality of structured electronic health records using a representation machine learning model. The memory instructs the processor to generate a diagnostic label as a function of the plurality of representations. The memory instructs the processor to display the diagnostic label using a display device.

Exemplary embodiments illustrating aspects of the present disclosure are described below in the context of several specific examples.

Electronic Health Records (EHR) provide a rich source of medical data across different modalities, such as Electrocardiograms (ECG), Patient Notes (Text) and structured EHR (structured EHR), which capture information about disease diagnoses, procedures, and medication prescriptions in the form of International Classification of Diseases (ICD) codes. In some cases, apparatus 100 may combine multi-modal data such as ECG, structured EHR and Text modalities to produce a plurality of representations of the combination of data. This plurality of representations may be used for a variety of downstream tasks. The plurality of representations may be compared against various versions of the plurality of representations. The comparison may be done using baseline models-supervised learning models trained from scratch with random initialization, currently available self-supervised learning models trained only on ECGs, and a supervised large scale multi-task learning model trained to perform both classification and regression tasks on a large number of diseases and lab test measurements. The machine learning models may be trained from a database comprising a large number ECGs, and evaluate the models on downstream tasks such as linear classification involving the prediction of various heart conditions, and demonstrate that the models presented in this work show significant improvements over all baseline models.

Figure 1:
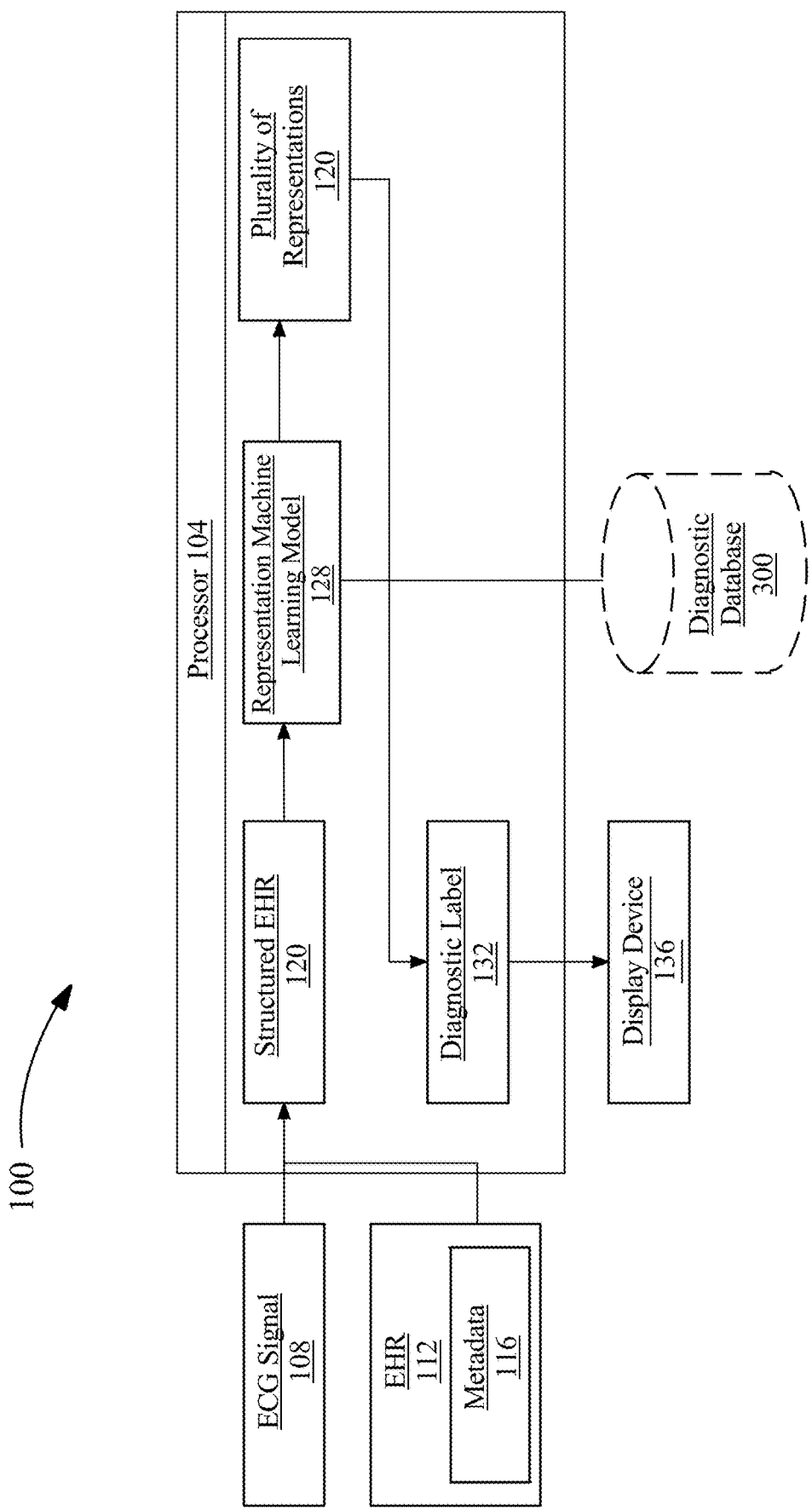
FIG. 1 is a block diagram of an exemplary embodiment of an apparatus for generating a diagnostic label.

Referring now to FIG. 1, an exemplary embodiment of an apparatus 100 for generating a diagnostic label is illustrated. Apparatus 100 includes a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of apparatus 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory. Memory is communicatively connected to processor 104. Memory may contain instructions configuring processor 104 to perform tasks disclosed in this disclosure. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, apparatus, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example, and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, without limitation, via a bus or other facility for intercommunication between elements of a computing device. Communicative connecting may also include indirect connections via, for example, and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, processor 104 is configured to receive a plurality of electrocardiogram (ECG) signals 108 from a user. As used in the current disclosure, a "electrocardiogram signal" is a signal representative of the electrical activity of the heart. The ECG signal 108 may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves provide information about the duration and regularity of various phases of the cardiac cycle. The ECG signal can help diagnose various heart conditions, such as arrhythmias, myocardial infarction (heart attack), conduction abnormalities, and electrolyte imbalances. In an embodiment, an each sensor may generate an individual ECG signal 108.

With continued reference to FIG. 1, the plurality of electrocardiogram signals 108 may be generated using at least a sensor. As used in this disclosure, a "sensor" is a device that is configured to detect an input and/or a phenomenon and transmit information related to the detection. Sensor may detect a plurality of data. A plurality of data detected by sensor may include, but is not limited to, electrocardiogram signals 108, heart rate, blood pressure, electrical signals related to the heart, and the like. In one or more embodiments, and without limitation, sensor may include a plurality of sensors. In one or more embodiments, and without limitation, sensor may include one or more electrodes, and the like. Electrodes used for an electrocardiogram (ECG) are small sensors or conductive patches that are placed on specific locations on the body to detect and record the electrical signals generated by the heart. Senor serves as the interface between the body and the ECG machine, allowing for the measurement and recording of the heart's electrical activity. A plurality of sensors may include 10 electrodes used for a standard 12-lead ECG, placed in specific positions on the chest and limbs of the patient. These electrodes are typically made of a conductive material, such as metal or carbon, and are connected to lead wires that transmit the electrical signals to the ECG machine for recording. Proper electrode placement is crucial to ensure accurate signal detection and recording.

With continued reference to FIG. 1, the plurality of sensors may be placed on each limb, wherein there may be at least one sensor on each arm and leg. These sensors may be labeled I, II, III, V1, V2, V3, V4, V5, V6, and the like. For example, Sensor I may be placed on the left arm, Sensor II may be placed on the right arm, and Sensor III may be placed on the left leg. Additionally, a plurality of sensors may be placed on various portions of the patient's torso and chest. For example, a sensor V1 may be placed in the fourth intercostal space at both the right sternal borders and sensor V2 may be fourth intercostal space at both the left sternal borders. A sensor V3 may also be placed between sensors V2 and V4, halfway between their positions. Sensor V4 may be placed in the fifth intercostal space at the midclavicular line. Sensor V5 may be placed horizontally at the same level as sensor V4 but in the anterior axillary line. Sensor V6 may be placed horizontally at the same level as V4 and V5 but in the midaxillary line.

With continued reference to FIG. 1, the plurality of sensors may include augmented unipolar sensors. These sensors may be labeled as aVR, aVL, and aVF. These sensor may be derived from the limb sensors and provide additional information about the heart's electrical activity. These leads are calculated using specific combinations of the limb leads and help assess the electrical vectors in different orientations. For example, aVR may be derived from Sensor II and Sensor III. In another example, aVL may be derived from sensor I and Sensor III. Additionally, aVF may be derived from Lead I and Lead II. The combination of limb sensors, precordial sensors, and augmented unipolar sensors allows for a comprehensive assessment of the heart's electrical activity in three dimensions.

With continued reference to FIG. 1, processor 104 is configured to receive a plurality of electronic health records (EHR) 112. As used in the current disclosure, "electronic health record" is a data structure which includes a collection of a health data associated with the user. As used in the current disclosure, "health data" refers to the collection of information related to a patient's health and healthcare. Health data may include elements of data regarding treatment records, medical history, laboratory results, radiology reports, medical records, clinical notes, and the like. An electronic health record (EHR) 112 is a digital version of a patient's medical information that is stored and managed in a computerized system. It is a comprehensive, longitudinal collection of a patient's health-related data that includes medical history, diagnoses, medications, treatment plans, test results, and other relevant health information. EHRs 112 contain a wide range of patient information, including personal demographics, medical history, allergies, immunizations, medications, laboratory results, imaging reports, surgical procedures, and progress notes. This comprehensive data provides a complete overview of a patient's health and facilitates informed decision-making. EHRs 112 may include a patient's past and current medical conditions, surgeries, allergies, immunization records, medications, and any significant health events. EHRs 112 may additionally include a large amount of information regarding the patient's health background. This may include previous diagnosis, medical tests, medical imaging, and the like. EHRs may include documentation, observations, assessments, and treatment plans from medical professionals. This may include progress notes, discharge summaries, and other relevant clinical documentation. EHRs may include information related to prescribed medications, including dosage, frequency, symptoms, effect, and duration. EHRs may include test results, which may include laboratory test results, radiology reports, medical imaging reports, and other diagnostic imaging findings.

With continued reference to FIG. 1, a EHRs 112 may be received by processor 104 via user input. For example, and without limitation, the user or a third party may manually input EHRs 112 using a graphical user interface of processor 104 or a remote device, such as for example, a smartphone or laptop. EHRs 112 may additionally be generated via the answer to a series of questions. The series of questions may be implemented using a chatbot, as described herein below. A chatbot may be configured to generate questions regarding any element of the EHRs 112. In a non-limiting embodiment, a user may be prompted to input specific information or may fill out a questionnaire. In an embodiment, a graphical user interface may display a series of questions to prompt a user for information pertaining to the EHRs 112. The EHRs 112 may be transmitted to processor 104, such as via a wired or wireless communication, as previously discussed in this disclosure.

With continued reference to FIG. 1, plurality of EHRs 112 may include a plurality of metadata 116. As used in the current disclosure, "metadata" refers to descriptive information or attributes that provide context, structure, and meaning to data. Metadata 116 is essentially data about data. Metadata 116 helps in understanding and managing various aspects of data, such as its origin, content, format, quality, and usage. It plays a crucial role in organizing, searching, and interpreting data effectively. Metadata 116 may include descriptive metadata, structural metadata, administrative metadata, technical metadata, provenance metadata, usage metadata, and the like. Metadata 116 may be organized and managed through metadata schemas, standards, or frameworks. These provide guidelines and specifications for capturing, storing, and exchanging metadata in a consistent and structured manner. Common metadata standards include Dublin Core, Metadata Object Description Schema (MODS), and the Federal Geographic Data Committee (FGDC) metadata standard. In some cases, metadata 116 may be associated with textual data or image data, both are discussed in greater detail herein below. In some cases, metadata 116 may include data associated with the health of the patient and the patient's medical records. Metadata 116 includes patient-specific information such as unique identifiers (e.g., medical record number, national identification number), patient demographics (name, date of birth, gender), contact details, and emergency contact information. These identifiers help in linking and identifying the EHR 112 of individual patients. Each entry or update in an EHR 112 is typically accompanied by a date and time stamp. This metadata 116 captures when the event or documentation took place, allowing healthcare providers to track the chronological order of patient encounters, treatments, test results, and other relevant information. Metadata 116 may include details about the healthcare professional or user who created or updated a specific EHR entry 112. This information may include the name, credentials, role, and department of the author. It helps in accountability, audit trails, and ensuring data integrity. Metadata 116 may indicate the source of the EHR data, whether it was entered directly by a healthcare provider, imported from a laboratory or diagnostic system, received from external healthcare organizations, or captured through patient-generated sources (e.g., wearables, patient-reported data). Metadata 116 may include information regarding access permissions, user roles, and security settings associated with the EHR 112. This metadata 116 may be used to enforce privacy and security protocols, ensuring that only authorized individuals can view, modify, or access specific portions of the EHR. Metadata 116 may contain notes, comments, or observations made by a medical professional. These annotations might highlight specific features, anomalies, or noteworthy aspects of the EHR 112. The date and time when the slide was prepared, analyzed, or labeled can be associated as metadata.

With continued reference to FIG. 1, the EHR 112 may include a plurality of multi-modal data associated with a user. As used in the current disclosure, "multi-modal data" is data which includes a plurality of modalities data. Modalities of data may include images, text, audio, documents, electronic health records, sensor data, and the like. Multi-modal data may include textual data. As used in the current disclosure, "textual data" is a collection of data that consists of text-based information. Textual data may include any written information, such as documents, emails, notes, handwriting, chat conversations, and the like. Examples of textual data may include documents, captions, sentences, paragraphs, free-text fields, transcriptions, prognostic labels, and the like. Textual data may include data a plurality of digital or hand written notes. Notes may be written by a medical professional. The notes may depict conditions of the patient. Textual data may be associated with electronic health records (EHRs). Textual data may refer to the written or typed information that is recorded and stored as part of a patient's health record in a digital format. It includes a wide range of textual information that provides details about the patient's medical history, diagnoses, treatments, procedures, medications, observations, clinical notes, and other relevant healthcare information. Multi-modal data may include image data. As used in the current disclosure, "image data" is a collection of data that consists of data associated with a plurality of images. Image data encompasses visual representations captured through cameras or generated through medical imaging, graphs, microscopes, or other image capturing systems. Image data associated with electronic health records (EHRs) refers to the visual information that is linked or integrated with the patient's health record. It includes medical images such as X-rays, CT scans, MRI scans, ultrasound images, endoscopy images, pathology slides, and other types of diagnostic or clinical images.

Still referring to FIG. 1, processor 104 may use optical character recognition or optical character reader (OCR) includes automatic conversion of images of written (e.g., typed, handwritten or printed text) into machine-encoded text. Images of written or printed text may be included in image data, textual data, or any other data mentioned throughout this disclosure. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases. a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 1, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning process like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIGS. 2 and 4-5. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool include OCRopus. OCRopus development is led by German Research Centre for Artificial Intelligence in Kaiserslautern, Germany. In some cases, OCR software may employ neural networks, for example neural networks as taught in reference to FIGS. 2 and 4-5.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 1, processor 104 may be configured to generate structured electronic health records 120 (structured EHR or sEHR) as a function of the electronic health records 112 (EHRs). As used in the current disclosure, "structured electronic health records" is a type of electronic health record where the data is organized in a structured format using standardized terminology and data models. Structured EHRs 120 may be represented by a plurality of diagnostic codes associated with the health data of the EHR 112, discussed in greater detail herein below. In structured EHRs 120, data is captured and stored using predefined data fields, codes, and standardized terminologies. This structured approach allows for consistency, interoperability, and ease of data retrieval and analysis. Structured EHRs 120 may follow a consistent and uniform structure, enabling easy data retrieval and analysis. They typically include fields or specific sections for patient demographics, medical history, medication details, allergies, vital signs, laboratory results, diagnoses, procedures, treatment plans, and the like. Structured EHRs 120 may follow standardized data models and formats, such as HL7 (Health Level 7) or CDA (Clinical Document Architecture). Structured EHRs 120 may use standardized medical terminologies, such as SNOMED CT (Systematized Nomenclature of Medicine-Clinical Terms) and LOINC (Logical Observation Identifiers Names and Codes), to ensure uniformity in data representation. This facilitates better communication, data analysis, and decision support.

With continued reference to FIG. 1, processor 104 may generate a structured electronic health records 120 by classifying health data in a plurality of diagnostic codes. As used in the current disclosure, "diagnostic codes" are a plurality of codes classification of diseases, injuries, and other health conditions. The diagnostic codes may include a numerical or an alphanumeric code that represents various portions of the user medical history. In an embodiment, diagnostic codes may include variations or combinations of ICD diagnoses codes, ICD procedure codes. and medication prescriptions used in the International Classification of Diseases (ICD) to classify and categorize medical diagnoses. Health data may be assigned one or more diagnostic codes as a function of the content of the health data. Each diagnostic code may include a corresponding medical code, time code, and medical code type. Time codes within the diagnostic codes may represent the medical conditions of the user within a given time period. For example, the time codes associated with the user may be generated weekly according to health conditions and/or treatments the user has experienced during that week. Medical codes may be divided into 10 or more categories. For Example, medical code categories may represent categories associated with Special Tokens, Diseases, Symptoms, Pregnancy/Congenital External/Others; Cardiac CPT procedures Non-cardiac CPT procedures PCS codes, HCPCS codes, Medication generic names, and the like. The diagnostic codes may follow a hierarchical structure, with codes organized into chapters, sections, and categories, facilitating easy navigation and identification of specific conditions. Diagnostic codes may utilize an alphanumeric format, typically consisting of three to seven characters, offering a range of specificity and clinical detail. Diagnostic codes may provide granularity and specificity, allowing for the precise description of diseases and health conditions. Diagnostic codes may be received from database 300.

With continued reference to FIG. 1, processor 104 may generate structured electronic health records 120 using a structure classifier. As used in the current disclosure, a "Structure classifier" is a classifier that is configured to generate structured electronic health records 120. Structure classifier may be consistent with the classifier described below in FIG. 2. Inputs to the Structure classifier may include EHR 112, Health Data, Metadata 116, diagnostic codes, examples of structured electronic health records 120, and the like. Outputs to the structure classifier may include structured electronic health records 120. Structure classifier may be configured to classify the plurality of health data to diagnostic codes. Structure training data may include a plurality of data entries containing a plurality of inputs that are correlated to a plurality of outputs for training a processor by a machine-learning process. In an embodiment, Structure training data may include a plurality of health data correlated to diagnostic codes. Additionally, structure training data may include health data and diagnostic codes correlated to examples of structured electronic health records 120. Structure training data may be received from database 300. Structure training data may contain information about EHR 112, Health Data, Metadata 116, diagnostic codes, examples of structured electronic health records 120, and the like. In an embodiment, Structure training data may be iteratively updated as a function of the input and output results of past Structure classifier or any other classifier mentioned throughout this disclosure. The classifier may use, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifier.

With continued reference to FIG. 1, processor 104 is configured to generate a plurality of representations 124 as a function of the plurality of electrocardiogram signals 108 and the structured electronic health records 120. As used in the current disclosure, a "plurality of representations" refers to the relationship or connection established between two or more elements of data. A plurality of representations 124 may be a representation of a plurality of data associated with the electrocardiogram signals 108 and structured electronic health records 120. A plurality of representations 124 may include a parametric map that takes high dimensional raw data and abstracts it into a lower dimensional feature vector that ideally encapsulates the essential information. The plurality of representations 124 may involve linking or integrating the ECG signal 108 with the descriptive or explanatory multi-modal data to provide additional context, enhance understanding, and convey relevant information. In an embodiment, the plurality of representations 124 may include a relationship or connection between an ECG signal 108 and an EHR 112. In another embodiment, the plurality of representations 124 may include a relationship or connection between an ECG signal 108 and structured EHR 120. Additionally, the plurality of representations 124 may include a relationship or connection between an ECG signal 108, structured EHR 120, and textual data. The plurality of representations 124 may include a longitudinal record of a patient's health history. By linking the ECG signal 108 to the plurality of multi-modal data, processor 104 can track and analyze the cardiac health of the patient over time. This longitudinal perspective enables the identification of trends, changes, or patterns in the ECG signal, aiding in the detection of cardiac abnormalities or changes in the patient's cardiovascular health.

With continued reference to FIG. 1, a plurality of representations 124 may be represented in vector form. A vector representing a plurality of representations 124 is a mathematical construct that can be used to represent multiple data points or variables. In the context of healthcare or any other domain, a vector can be constructed to capture and represent a diverse set of data points. A vector has a certain number of dimensions, which may correspond to the number of data points or variables being represented. Each dimension in the vector corresponds to a specific data point or variable. Each dimension in the vector represents a distinct data point or variable. For example, in the healthcare domain, these data points could include patient demographics (e.g., age, gender), medical history (e.g., conditions, surgeries), laboratory results (e.g., cholesterol levels, glucose levels), vital signs (e.g., blood pressure, heart rate), or any other relevant healthcare-related information. Values within each dimension of the vector, there are corresponding values that represent the specific data point or variable. These values can be numerical, categorical, or symbolic, depending on the nature of the data being represented. In an embodiment, the plurality of representations 124 represented as a vector may be used to convey a large amount of information regarding the patient. This may include information regarding the ECG signal 108, Multi-modal data, health data, structured EHR 120, and the like. In a non-limiting example, a representation 124 in vector form may represent all or part of the amplitude, time, waveforms, heart rate, and rhythm of the ECG signal 108. Additionally, a representation 124 in vector form may represent all or part of patient demographics, medical history, past and present diagnosis, past and present medical procedures, Medications, laboratory results, clinical notes. A plurality of representations 124 in vector form may represent the diagnostic codes of the structured EHR 120. For example, the dimensions of the vector may correspond to the number of diagnostic codes being represented, wherein each dimension may represent a specific diagnostic code.

With continued reference to FIG. 1, a plurality of representations 124 may include a first representation, second representation, and/or a third representation. Each representation of the plurality of representations may be depicted as a vector. As used in the current disclosure, a "first representation" refers to the relationship or connection established between the plurality of electrocardiogram signals 108, textual data, and the structured EHR 112. The representation of ECG signals with the structured EHR, along with textual data, may enhance decision-making and care coordination. Healthcare professionals can utilize the combined information to make more informed diagnoses, develop appropriate treatment plans, monitor patient progress, and ensure continuity of care. The availability of both ECG signals and textual data in a unified system promotes seamless communication and collaboration among healthcare teams involved in the patient's care As used in the current disclosure, a "second representation" refers to the relationship or connection established between the plurality of electrocardiogram signals 108 and the structured EHR 120. The recorded ECG signals 108 may be integrated into the structured EHR. This integration ensures that the ECG signal 108 becomes a part of the patient's longitudinal health record, enabling healthcare professionals to access and analyze it alongside other health information. As used in the current disclosure, a "third representation" includes refers to the relationship or connection established between the plurality of electrocardiogram signals 108 and textual data. Each representation of the plurality of representations 124. ECG signals 108 are often interpreted by healthcare providers, such as cardiologists or electrocardiography technicians, who analyze the signals to diagnose cardiac abnormalities or conditions. Their findings, assessments, and interpretations are documented in textual format within the SEHR 120. The textual data may include descriptions of the ECG waveforms, identification of abnormalities, diagnostic conclusions, and recommended treatment plans.

With continued reference to FIG. 1, processor 104 may generate a plurality of representations 124 using a representation machine-learning model 128. As used in the current disclosure, a "representation machine machine-learning model" is a machine-learning model that is configured to generate a plurality of representations 124. The representation machine machine-learning model may be consistent with the machine-learning model or classifier described below in FIG. 2. Inputs to the representation machine machine-learning model may include an ECG signal 108, EHR 112, plurality of metadata 116, structured EHR 120, a plurality of diagnostic codes, examples of a plurality of representations 124, and the like. Outputs to the representation machine machine-learning model may include a plurality of representations 124. Outputs to the representation machine-learning model 128 may also include a first representation, a second representation, and third representation. The representation machine-learning model 128 may be configured to generate representations of data from several different modalities. Representation training data may include a plurality of data entries containing a plurality of inputs that are correlated to a plurality of outputs for training a processor by a machine-learning process. In an embodiment, representation training data may include a plurality of structured electronic health records 120 and ECG Signals 108 correlated to examples of a plurality of representations 124. In other embodiments, representation training data may include a plurality of structured electronic health records 120, ECG Signals 108, and textual data correlated to examples of a first representations. Additionally, representation training data may include a plurality of structured electronic health records 120 and textual data correlated to examples of a third representations. Representation training data may be received from database 300. Representation training data may contain information about ECG signal 108, EHR 112, plurality of metadata 116, structured EHR 120, a plurality of diagnostic codes, examples of a plurality of representations 124, and the like. In an embodiment, representation training data may be iteratively updated as a function of the input and output results of past representation machine machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model, and the like.

With continued reference to FIG. 1, processor 104 may be configured to assign at least one diagnostic label 132 to the user and/or user profile 128 as a function of the plurality of representations 124. As used in the current disclosure, a "diagnostic label" is a label used describe a specific condition, disorder, or illness that affects an individual's health. A diagnostic label 132 may be associated any specific condition, disorder, or illness, associated with the heart. In a non-limiting example, diagnostic labels 132 may be associated with conditions related to the cardiac health such as Atherosclerotic cardiovascular disease (ASCVD), Myocarditis, Pulmonary Hypertension (PH), Left ventricular ejection fraction (LVEF), Atrial fibrillation in Normal Sinus Rhythm (AFib in NSR), and the like. Processor 104 may assign a diagnostic label 132 to user as function of the comparison of the. Processor 104 may assign a diagnostic label 132 by comparing the current representations 124 to similar representations from other users. The comparison may include comparing the size, location, magnitude, and the like of the representation 124 to similar representations from other similarly situated patients. This may also be cross referenced with a user profile, wherein the user profile may provide additional context for the comparison. Processor 104 may employ pattern matching techniques to identify specific patterns or abnormalities within the plurality of representations 124 to generate diagnostic label 132. This can involve comparing specific segments, intervals, or waveforms of the ECG signal to detect similarities or differences. Cross-correlation, template matching, or dynamic time warping algorithms may be used for this purpose. Processor 104 may perform statistical analysis on various parameters derived from the plurality of representations 124 to generate diagnostic label 132. This can involve calculating means, standard deviations, or other statistical measures for specific features or segments of the plurality of representations 124. By comparing these statistical parameters, the processor can identify significant differences or similarities between the plurality of representations 124.

With continued reference to FIG. 1, processor 104 may generate a diagnostic label using a diagnostic machine-learning model. As used in the current disclosure, an "diagnostic machine-learning model" is a machine-learning model that is configured to assign a diagnostic label 132 to a user. Diagnostic machine-learning model may be consistent with the machine-learning model described below in FIG. 2. Inputs to the diagnostic machine-learning model may include an ECG signal 108, EHR 112, plurality of metadata 116, structured EHR 120, a plurality of diagnostic codes, a plurality of representations 124, examples of diagnostic label 132, and the like. Outputs to the diagnostic machine-learning model may include assigning a diagnostic label 132 tailored to the plurality of representations 124. Diagnostic training data may include a plurality of data entries containing a plurality of inputs that are correlated to a plurality of outputs for training a processor by a machine-learning process. In an embodiment, diagnostic training data may include a plurality of representations 124 correlated to examples diagnostic label 132. Diagnostic training data may be received from database 300. Diagnostic training data may contain information about ECG signal 108, EHR 112, plurality of metadata 116, structured EHR 120, a plurality of diagnostic codes, a plurality of representations 124, examples of diagnostic label 132, and the like. In an embodiment, diagnostic training data may be iteratively updated as a function of the input and output results of past diagnostic machine-learning model or any other machine-learning model mentioned throughout this disclosure. The machine-learning model may be performed using, without limitation, linear machine-learning models such as without limitation logistic regression and/or naive Bayes machine-learning models, nearest neighbor machine-learning models such as k-nearest neighbors machine-learning models, support vector machines, least squares support vector machines, fisher's linear discriminant, quadratic machine-learning models, decision trees, boosted trees, random forest machine-learning model.

Still referring to FIG. 1, the processor may be configured to generate a machine-learning model, such as diagnostic machine-learning model, using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P (A/B)=P (B/A) P (A)+P (B), where P (A/B) is the probability of hypothesis A given data B also known as posterior probability; P (B/A) is the probability of data B given that the hypothesis A was true; P (A) is the probability of hypothesis A being true regardless of data also known as prior probability of A; and P (B) is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

Still referring to FIG. 1, processor 104 may be configured to generate a machine-learning model, such as diagnostic machine-learning model, using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm $$l = \sqrt{\sum_{i=0}^{n} a_i^2},$$

where $a_i$ is attribute number experience of the vector. Scaling and/or normalization may function to make vector comparison independent of absolute quantities of attributes, while preserving any dependency on the similarity of attributes; this may, for instance, be advantageous where cases represented in training data are represented by different quantities of samples, which may result in proportionally equivalent vectors with divergent values.

With continued reference to FIG. 1, processor 104 may generate a diagnostic report based on the assignment of one or more diagnostic labels 132. As used in the current disclosure, a "diagnostic report" is a comprehensive summary of the analysis performed on the plurality of representations 124 and the resulting assignment of one or more diagnostic labels 132. A diagnostic report describes essential patient information, such as the patient's name, age, sex, and any relevant medical identifiers. This information ensures proper identification of the patient and helps to associate the diagnostic findings with the correct individual. The diagnostic report may include the date and time of the recording of the ECG signals 108, the signal or electrode configuration employed, and any specific instructions or conditions during the recording process. These details provide context for the subsequent analysis and interpretation. The report may include technical findings related to the quality and validity of the plurality of representations 124. This can involve observations or notes about signal quality, or any technical issues that may have influenced the analysis. These findings help to assess the reliability of the diagnostic conclusions. The report may include the diagnostic features from the plurality of representations 124, along with other features such as loops, loop orientation, loop shape, QRS complex characteristics, ST-segment abnormalities, and the like. The report may provide numerical values, graphical representations, or visual illustrations of these features to aid in understanding. Based on the analysis of the diagnostic features, the report may include diagnostic conclusions associated with the diagnostic labels 132. It identifies any abnormalities or specific cardiac conditions present in the plurality of representations 124. The diagnostic conclusions can be binary (normal vs. abnormal) or multiclass labels representing different cardiac conditions. Each conclusion is supported by the analysis of the extracted features and may include a confidence level or severity assessment.

With continued reference to FIG. 1, processor 104 may be configured to generate a plurality of graphical data as a function of the plurality of representations 124. As used in the current disclosure, "graphical data" is a visual representation of information that conveys aspects of the plurality of representations 124. Graphical data may refer to any type of data that is presented visually through graphical representations, such as charts, graphs, diagrams, maps, and other visual aids. These visual representations may represent complex data and are used to communicate information in a way that is easier to comprehend. Graphical data can come in many forms, depending on the type of data being presented and the intended audience. For example, a line graph may be used to show the trend of a particular data set over time, while a pie chart may be used to display the distribution of different categories within a larger data set. Other types of graphical data may include bar charts, scatter plots, heat maps, network diagrams, and the like. Graphical data may include a graphical representation of one or more elements of a first representation, a second representation, or a third representation. In an embodiment, graphical data may include a graphical representation of the plurality of representations 124 associated with the current patient. Additionally graphical data may include a graphical representation of a plurality of representations 124 associated with past patients. The representations associated with past patients may be generated from database 300. Graphical data may include a graphical representation of the plurality of representations 124 in vector form. In some embodiments, graphical data may include plotting plurality of representations 124 along a continuum. As used in the current disclosure, a "continuum" is a spectrum or a range of values, qualities, or attributes that exist along a single dimension or scale. A continuum may represent a continuous progression from one extreme to another, without any clear-cut boundaries or discrete categories. In a continuum, there are no distinct breakpoints or divisions, instead, there is a gradual transition or progression from one end to the other. In some embodiments, a continuum may represent qualitative traits that exist on a spectrum. In a non-limiting example, a continuum may represent one or more characteristics associated with the structured ECG 120, Textual data, multimodal data, ECG signal 108. Graphical data may include a plurality of continuums, wherein each continuum represents one more trait or characteristics of the representations. In some embodiments, multiple continuums may be combined to generate an XY plot or an XYZ plot. Processor 104 may be configured to add labels to the axes, a title, legends, and any other visual elements that provide context to graphical data. Processor 104 may additionally be configured to customize the appearance of data points, lines, or other graphical elements. In order to plot the graphical data processor 104 may be configured to organize the plurality of representations 124 in a suitable format. In a non-limiting example, this may involve having two sets of values: the independent variable (x-values) representing the continuum or range, and the dependent variable (y-values) representing the corresponding to two aspects of the plurality of representations 124. Processor 104 may identify and implement a plotting library to generate graphical data. Examples of plotting libraries may include but are not limited to Matplotlib for Python, ggplot for R, or Plotly for JavaScript. Processor 104 may then Pass the x and y values to the plotting library's function dedicated to creating scatter plots or line plots. This will generate a plot with the data points representing various aspects of the plurality of representations 124 along the continuum.

With continued reference to FIG. 1, graphical data includes one or more representation clusters. As used herein, a "representation cluster" is a collection of data points representing at least one attribute or characteristic of plurality of representations 124. A representation cluster may include a grouping of data points that represents a collection of similar or related data points within a dataset. In other words, a representation cluster is a subset of data points that exhibit some degree of similarity or proximity to each other, while being distinct from other clusters in the dataset. Identification of representation clusters may be used to uncover patterns, structure, or relationships within a dataset such as common traits or factors among patients with common diagnostic labels 132. Clusters can be formed based on various criteria, such as proximity in the feature space or similarity in attributes. By identifying clusters, processor 104 may gain insights into the underlying structure of the data and potentially discover meaningful patterns or subgroups within plurality of representations 124. Representation clusters may include a single attribute of the user, or they may include more than one attribute. Representation clusters may include multiple related attributes. In a non-limiting example, a representation clusters may include a plurality of data points representing the a characteristic of an ECG signal 108 along with patient specific attributes such medical history. Processor 104 may identify an representation cluster based on their similarity or homogeneity as it relates to the group of data points. An representation cluster may represent groups of data points that share similar characteristics or properties. For example, a representation cluster may represent group of patients with similar ECG signals 108 or similar traits indicated within their SEHR 120 such as a medical history. In some cases, a processor 104 may identify grouping and subgroupings based on the identification of one or more representation clusters 124. Representation clusters 124 may indicate the existence of distinct subpopulations or classes within the dataset. Clusters can reveal patterns or structures in the data that are not immediately apparent. By examining the characteristics of data points within a cluster, we may uncover relationships or associations that can be useful for further analysis or decision-making. For a non-limiting example, a representation cluster may represent a group of patients who are at high risk for ischemic heart disease and who have had a medical history of this illness in their family. Processor 104 may compare the representation clusters 124 the current cohort of patients to the national averages or national databases to gain additional insights.

Still referring to FIG. 1, processor 104 may be configured to display the diagnostic label 132 using a display device 136. As used in the current disclosure, a "display device" is a device that is used to display content. A display device 136 may include a user interface. A "user interface," as used herein, is a means by which a user and a computer system interact; for example, through the use of input devices and software. A user interface may include a graphical user interface (GUI), command line interface (CLI), menu-driven user interface, touch user interface, voice user interface (VUI), form-based user interface, any combination thereof, and the like. A user interface may include a smartphone, smart tablet, desktop, or laptop operated by the user. In an embodiment, the user interface may include a graphical user interface. A "graphical user interface (GUI)," as used herein, is a graphical form of user interface that allows users to interact with electronic devices. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull down menu. When any option is clicked in this menu, then the pull down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. Information contained in user interface may be directly influenced using graphical control elements such as widgets. A "widget," as used herein, is a user control element that allows a user to control and change the appearance of elements in the user interface. In this context a widget may refer to a generic GUI element such as a check box, button, or scroll bar to an instance of that element, or to a customized collection of such elements used for a specific function or application (such as a dialog box for users to customize their computer screen appearances). User interface controls may include software components that a user interacts with through direct manipulation to read or edit information displayed through user interface. Widgets may be used to display lists of related items, navigate the system using links, tabs, and manipulate data using check boxes, radio boxes, and the like.

Figure 2:
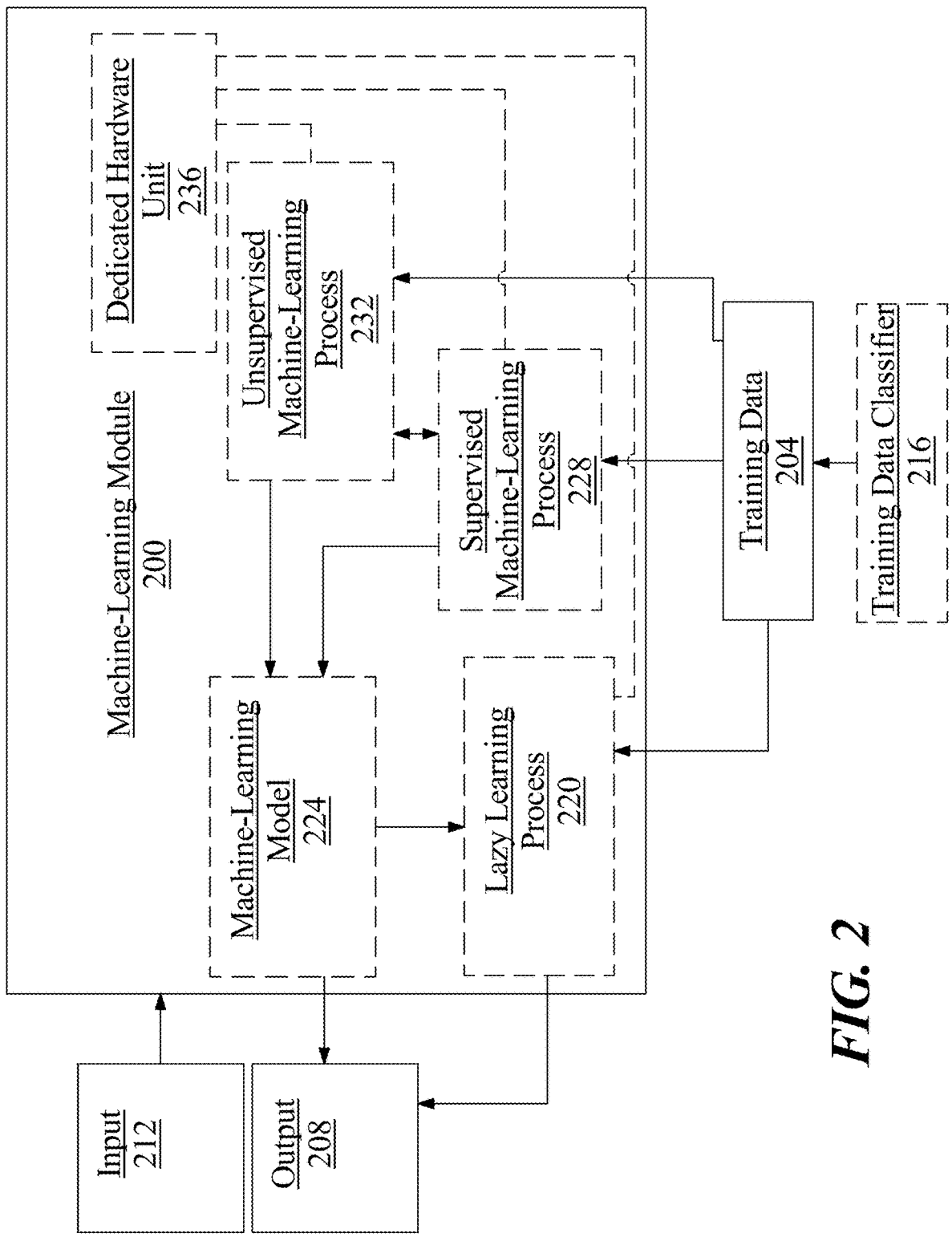
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example [describe inputs and outputs that might be used with invention].

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a processes whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify structured electronic health records 120 and ECG Signals 108 correlated to examples of a plurality of representations 124

With further reference to FIG. 2, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may identify as having poor quality data, where "poor quality" is defined as having a signal to noise ratio below a threshold value.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include structured electronic health records 120 and ECG Signals 108 as described above as inputs, plurality of representations 124 as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 232. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 232 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 232 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 232 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
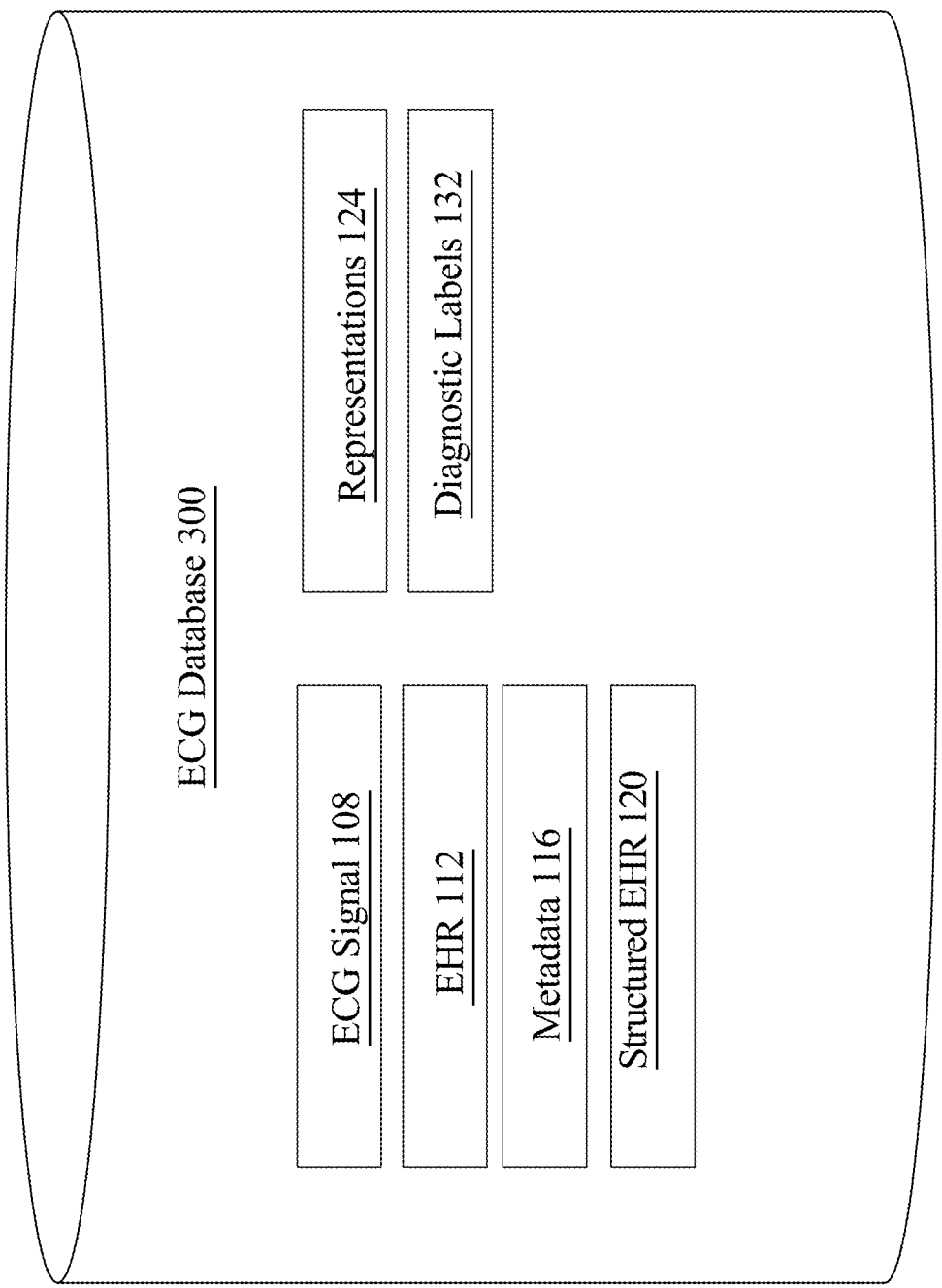
FIG. 3 is a block diagram of an exemplary embodiment of an electrocardiogram database.

Now referring to FIG. 3, an exemplary electrocardiogram database 300 is illustrated by way of block diagram. In an embodiment, any past or present versions of any data disclosed herein may be stored within the electrocardiogram database 300 including but not limited to: ECG signal 108, EHR 112, plurality of metadata 116, structured EHR 120, a plurality of diagnostic codes, a plurality of representations 124, diagnostic label 132, and the like. Processor 104 may be communicatively connected with electrocardiogram database 300. For example, in some cases, database 300 may be local to processor 104. Alternatively or additionally, in some cases, database 300 may be remote to processor 104 and communicative with processor 104 by way of one or more networks. Network may include, but not limited to, a cloud network, a mesh network, or the like. By way of example, a "cloud-based" system, as that term is used herein, can refer to a system which includes software and/or data which is stored, managed, and/or processed on a network of remote servers hosted in the "cloud," e.g., via the Internet, rather than on local severs or personal computers. A "mesh network" as used in this disclosure is a local network topology in which the infrastructure processor 104 connects directly, dynamically, and non-hierarchically to as many other computing devices as possible. A "network topology" as used in this disclosure is an arrangement of elements of a communication network. Electrocardiogram database 300 may be implemented, without limitation, as a relational database, a key-value retrieval database such as a NOSQL database, or any other format or structure for use as a database that a person skilled in the art would recognize as suitable upon review of the entirety of this disclosure. Electrocardiogram database 300 may alternatively or additionally be implemented using a distributed data storage protocol and/or data structure, such as a distributed hash table or the like. Electrocardiogram database 300 may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

Figure 4:
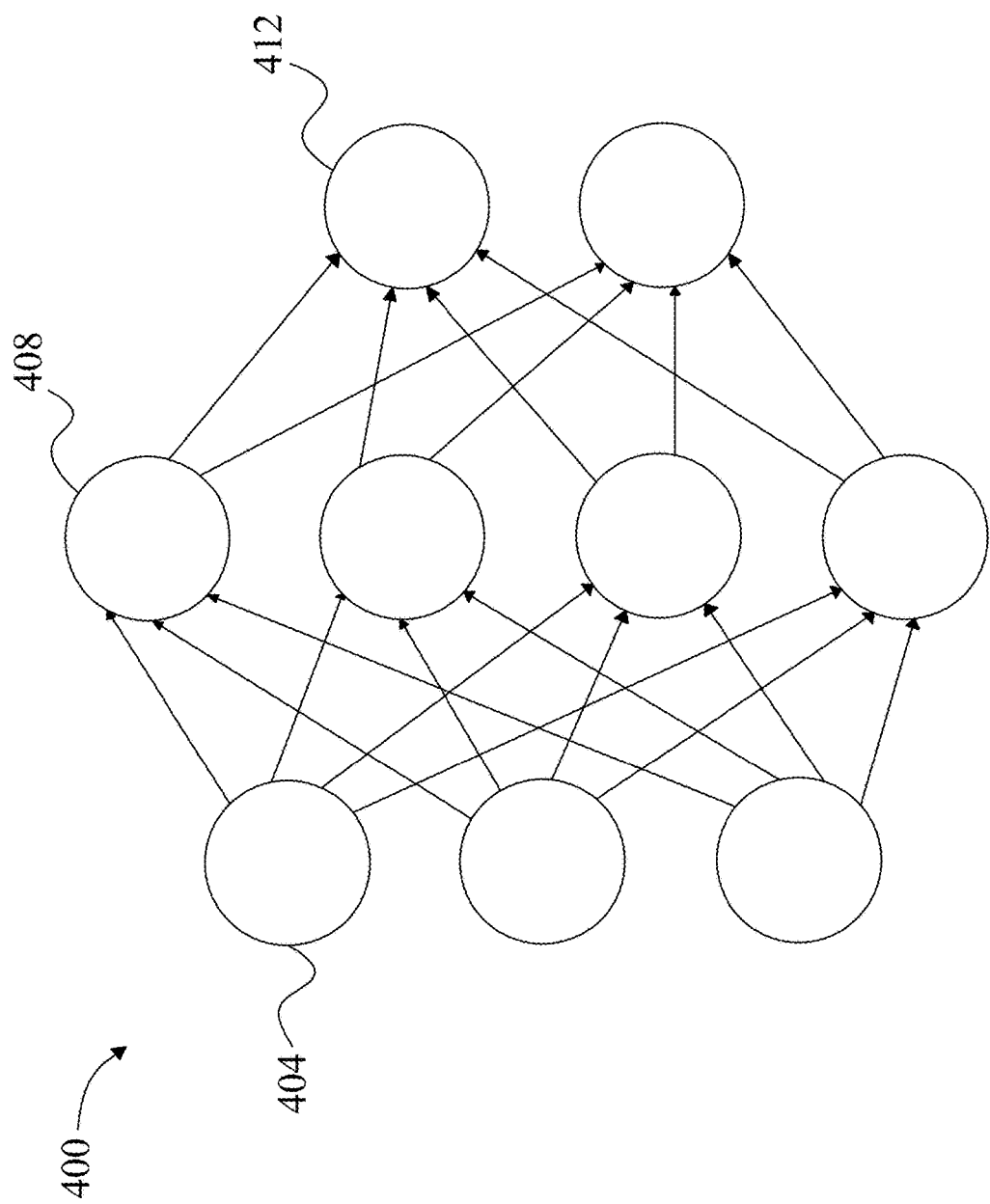
FIG. 4 is a diagram of an exemplary embodiment of a neural network.

Referring now to FIG. 4, an exemplary embodiment of neural network 400 is illustrated. A neural network 400 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 5:
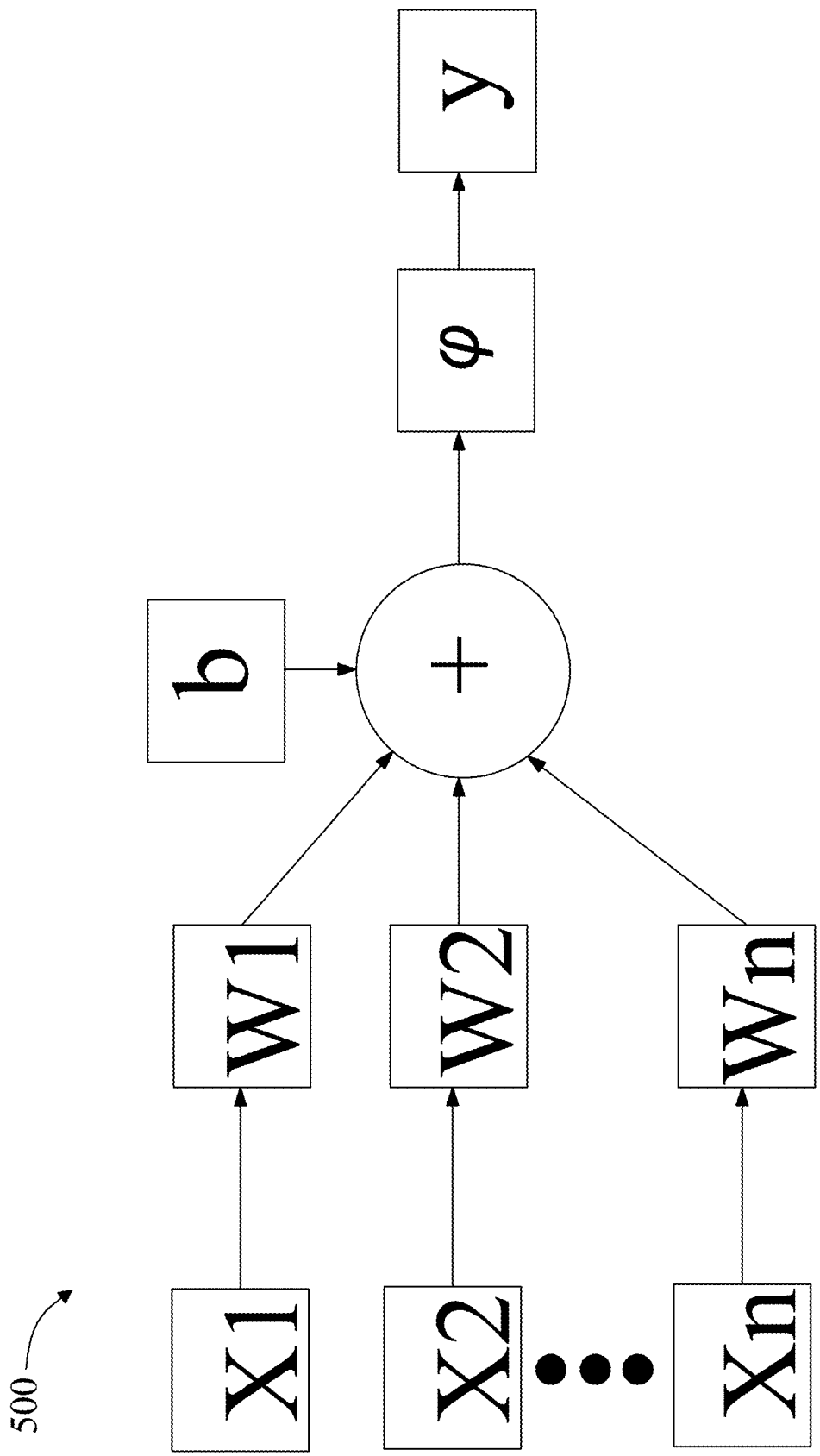
FIG. 5 is a diagram of an exemplary embodiment of a node of a neural network.

Referring now to FIG. 5, an exemplary embodiment of a node of a neural network is illustrated. A node may include, without limitation, a plurality of inputs x, that may receive numerical values from inputs to a neural network containing the node and/or from other nodes. Node may perform a weighted sum of inputs using weights w, that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$, applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 6:
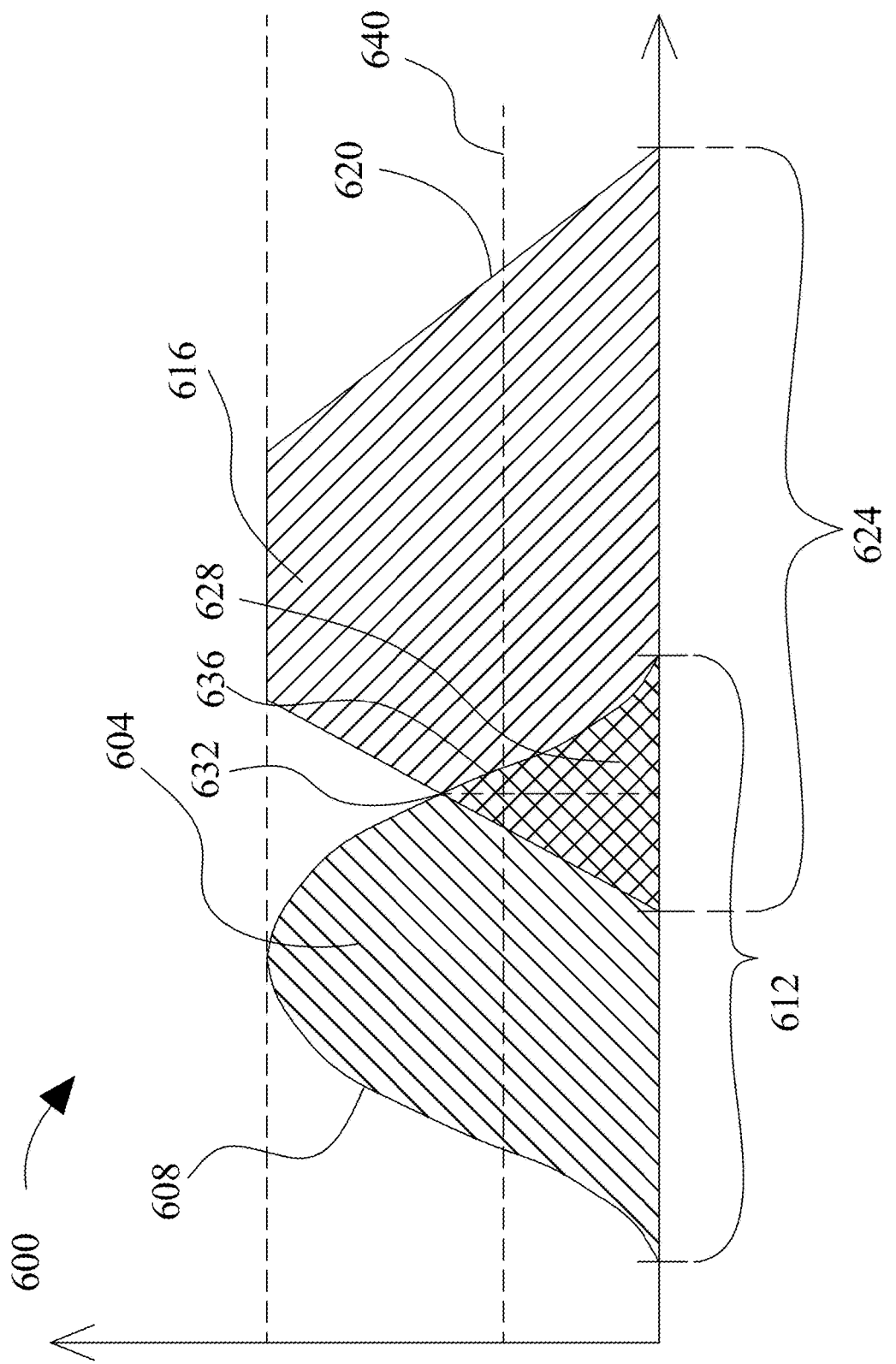
FIG. 6 is an illustration of an exemplary embodiment of fuzzy set comparison.

Now referring to FIG. 6, an exemplary embodiment of fuzzy set comparison 600 is illustrated. In a non-limiting embodiment, the fuzzy set comparison. In a non-limiting embodiment, fuzzy set comparison 600 may be consistent with fuzzy set comparison in FIG. 1. In another non-limiting the fuzzy set comparison 600 may be consistent with the name/version matching as described herein. For example, and without limitation, the parameters, weights, and/or coefficients of the membership functions may be tuned using any machine-learning methods for the name/version matching as described herein. In another non-limiting embodiment, the fuzzy set may represent a plurality of representations 124 and plurality of historical representations from FIG. 1.

Alternatively, or additionally, and still referring to FIG. 6, fuzzy set comparison 600 may be generated as a function of determining data compatibility threshold. The compatibility threshold may be determined by a computing device. In some embodiments, a computing device may use a logic comparison program, such as, but not limited to, a fuzzy logic model to determine the compatibility threshold and/or version authenticator. Each such compatibility threshold may be represented as a value for a posting variable representing the compatibility threshold, or in other words a fuzzy set as described above that corresponds to a degree of compatibility and/or allowability as calculated using any statistical, machine-learning, or other method that may occur to a person skilled in the art upon reviewing the entirety of this disclosure. In some embodiments, determining the compatibility threshold and/or version authenticator may include using a linear regression model. A linear regression model may include a machine learning model. A linear regression model may map statistics such as, but not limited to, frequency of the same range of version numbers, and the like, to the compatibility threshold and/or version authenticator. In some embodiments, determining the compatibility threshold of any posting may include using a classification model. A classification model may be configured to input collected data and cluster data to a centroid based on, but not limited to, frequency of appearance of the range of versioning numbers, linguistic indicators of compatibility and/or allowability, and the like. Centroids may include scores assigned to them such that the compatibility threshold may each be assigned a score. In some embodiments, a classification model may include a K-means clustering model. In some embodiments, a classification model may include a particle swarm optimization model. In some embodiments, determining a compatibility threshold may include using a fuzzy inference engine. A fuzzy inference engine may be configured to map one or more compatibility threshold using fuzzy logic. In some embodiments, a plurality of computing devices may be arranged by a logic comparison program into compatibility arrangements. A "compatibility arrangement" as used in this disclosure is any grouping of objects and/or data based on skill level and/or output score. Membership function coefficients and/or constants as described above may be tuned according to classification and/or clustering algorithms. For instance, and without limitation, a clustering algorithm may determine a Gaussian or other distribution of questions about a centroid corresponding to a given compatibility threshold and/or version authenticator, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Still referring to FIG. 6, inference engine may be implemented according to input a plurality of representations and a plurality historical representations. For instance, an acceptance variable may represent a first measurable value pertaining to the classification of a plurality of representations 124 to an plurality of historical representations. Continuing the example, an output variable may represent at least one diagnostic label 132. In an embodiment, a plurality of representations 124 and/or an plurality of historical representations may be represented by their own fuzzy set. In other embodiments, an evaluation factor may be represented as a function of the intersection two fuzzy sets as shown in FIG. 6, An inference engine may combine rules, such as any semantic versioning, semantic language, version ranges, and the like thereof. The degree to which a given input function membership matches a given rule may be determined by a triangular norm or "T-norm" of the rule or output function with the input function, such as min (a, b), product of a and b, drastic product of a and b, Hamacher product of a and b, or the like, satisfying the rules of commutativity (T(a, b)=T(b, a)), monotonicity: (T(a, b)≤T(c, d) if a≤c and b≤d), (associativity: T(a, T(b, c))=T(T(a, b), c)), and the requirement that the number 1 acts as an identity element. Combinations of rules ("and" or "or" combination of rule membership determinations) may be performed using any T-conorm, as represented by an inverted T symbol or "⊥," such as max (a, b), probabilistic sum of a and b (a+b−a*b), bounded sum, and/or drastic T-conorm; any T-conorm may be used that satisfies the properties of commutativity: ⊥(a, b)=⊥(b, a), monotonicity: ⊥(a, b)≤⊥(c, d) if a≤c and b≤d, associativity: ⊥(a, ⊥(b, c))=⊥(⊥(a, b), c), and identity element of 0. Alternatively, or additionally T-conorm may be approximated by sum, as in a "product-sum" inference engine in which T-norm is product and T-conorm is sum. A final output score or other fuzzy inference output may be determined from an output membership function as described above using any suitable defuzzification process, including without limitation Mean of Max defuzzification, Centroid of Area/Center of Gravity defuzzification, Center Average defuzzification, Bisector of Area defuzzification, or the like. Alternatively, or additionally, output rules may be replaced with functions according to the Takagi-Sugeno-King (TSK) fuzzy model.

A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{-\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

First fuzzy set 604 may represent any value or combination of values as described above, including any a plurality of representations 124 and plurality of historical representations. A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 636 that overlaps, first membership function 608 and second membership function 620 may intersect at a point 632 representing a probability, as defined on probability interval, of a match between first fuzzy set 604 and second fuzzy set 616. Alternatively, or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, the assignment of at least one diagnostic label 132 may indicate a sufficient degree of overlap with fuzzy set representing a plurality of representations 124 and an plurality of historical representations for combination to occur as described above. Each threshold may be established by one or more user inputs. Alternatively, or additionally, each threshold may be tuned by a machine-learning and/or statistical process, for instance and without limitation as described in further detail below.

In an embodiment, a degree of match between fuzzy sets may be used to rank one resource against another. For instance, if both a plurality of representations 124 and a plurality of historical representations have fuzzy sets, at least one diagnostic label 132 may be assigned by having a degree of overlap exceeding a predictive threshold, processor 104 may further rank the two resources by ranking a resource having a higher degree of match more highly than a resource having a lower degree of match. Where multiple fuzzy matches are performed, degrees of match for each respective fuzzy set may be computed and aggregated through, for instance, addition, averaging, or the like, to determine an overall degree of match, which may be used to rank resources; selection between two or more matching resources may be performed by selection of a highest-ranking resource, and/or multiple notifications may be presented to a user in order of ranking.

Figure 7:
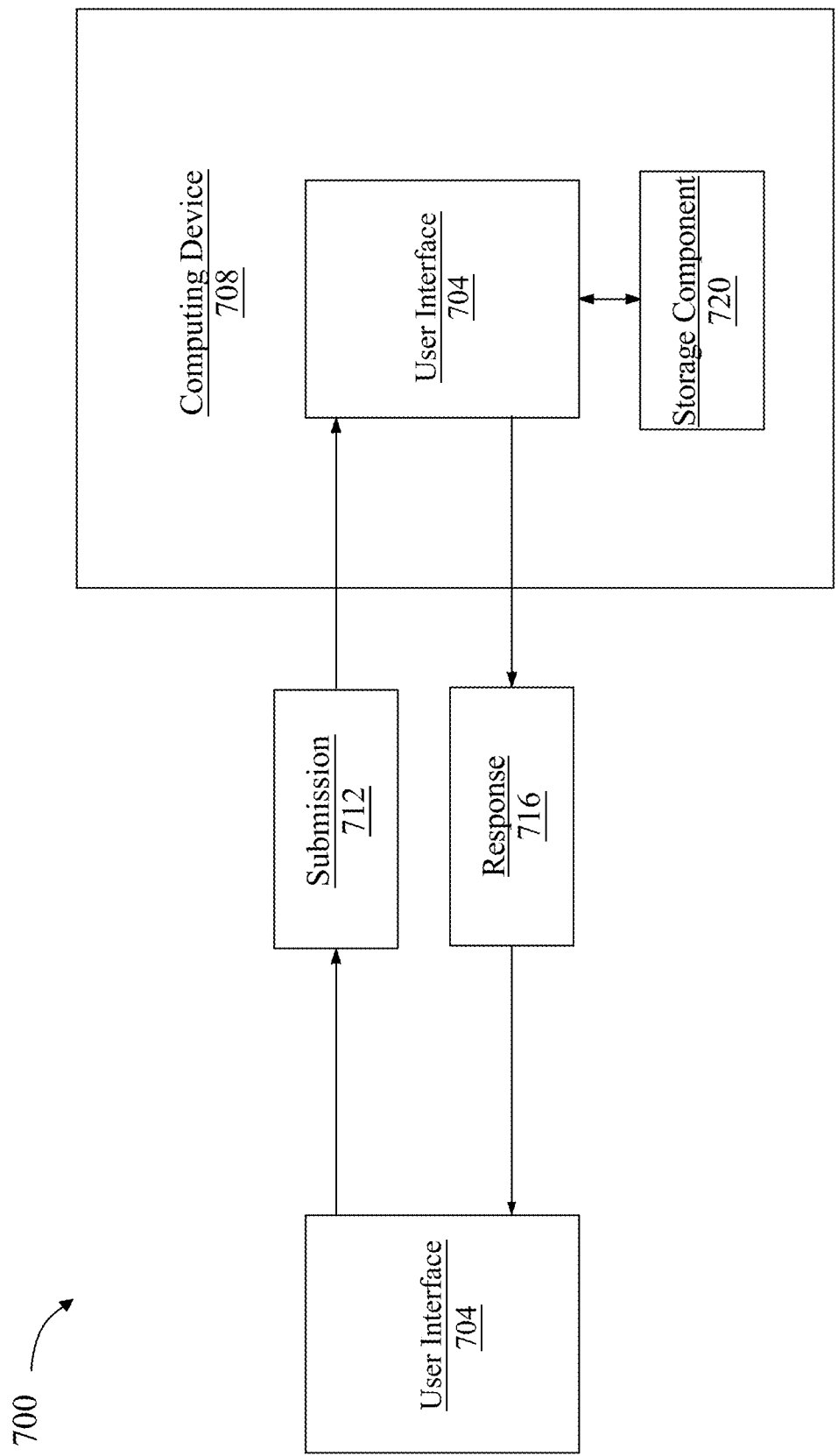
FIG. 7 is an illustration of an exemplary embodiment of a chatbot.

Referring to FIG. 7, a chatbot system 700 is schematically illustrated. According to some embodiments, a user interface 704 may be communicative with a computing device 708 that is configured to operate a chatbot. In some cases, user interface 704 may be local to computing device 708. Alternatively or additionally, in some cases, user interface 704 may remote to computing device 708 and communicative with the computing device 708, by way of one or more networks, such as without limitation the internet. Alternatively or additionally, user interface 704 may communicate with user device 708 using telephonic devices and networks, such as without limitation fax machines, short message service (SMS), or multimedia message service (MMS). Commonly, user interface 704 communicates with computing device 708 using text-based communication, for example without limitation using a character encoding protocol, such as American Standard for Information Interchange (ASCII). Typically, a user interface 704 conversationally interfaces a chatbot, by way of at least a submission 712, from the user interface 708 to the chatbot, and a response 716, from the chatbot to the user interface 704. In many cases, one or both of submission 712 and response 716 are text-based communication. Alternatively or additionally, in some cases, one or both of submission 712 and response 716 are audio-based communication.

Continuing in reference to FIG. 7, a submission 712 once received by computing device 708 operating a chatbot, may be processed by a processor. In some embodiments, processor processes a submission 712 using one or more of keyword recognition, pattern matching, and natural language processing. In some embodiments, processor employs real-time learning with evolutionary algorithms. In some cases, processor may retrieve a pre-prepared response from at least a storage component 720, based upon submission 712. Alternatively or additionally, in some embodiments, processor communicates a response 716 without first receiving a submission 712, thereby initiating conversation. In some cases, processor communicates an inquiry to user interface 704; and the processor is configured to process an answer to the inquiry in a following submission 712 from the user interface 704. In some cases, an answer to an inquiry present within a submission 712 from a user device 704 may be used by computing device 708 as an input to another function.

With continued reference to FIG. 7, A chatbot may be configured to provide a user with a plurality of options as an input into the chatbot. Chatbot entries may include multiple choice, short answer response, true or false responses, and the like. A user may decide on what type of chatbot entries are appropriate. In some embodiments, the chatbot may be configured to allow the user to input a freeform response into the chatbot. The chatbot may then use a decision tree, data base, or other data structure to respond to the users entry into the chatbot as a function of a chatbot input. As used in the current disclosure, "Chatbot input" is any response that a candidate or employer inputs in to a chatbot as a response to a prompt or question.

With continuing reference to FIG. 7, computing device 708 may be configured to the respond to a chatbot input using a decision tree. A "decision tree," as used in this disclosure, is a data structure that represents and combines one or more determinations or other computations based on and/or concerning data provided thereto, as well as earlier such determinations or calculations, as nodes of a tree data structure where inputs of some nodes are connected to outputs of others. Decision tree may have at least a root node, or node that receives data input to the decision tree, corresponding to at least a candidate input into a chatbot. Decision tree has at least a terminal node, which may alternatively or additionally be referred to herein as a "leaf node," corresponding to at least an exit indication; in other words, decision and/or determinations produced by decision tree may be output at the at least a terminal node. Decision tree may include one or more internal nodes, defined as nodes connecting outputs of root nodes to inputs of terminal nodes. Computing device 708 may generate two or more decision trees, which may overlap; for instance, a root node of one tree may connect to and/or receive output from one or more terminal nodes of another tree, intermediate nodes of one tree may be shared with another tree, or the like.

Still referring to FIG. 7, computing device 708 may build decision tree by following relational identification; for example, relational indication may specify that a first rule module receives an input from at least a second rule module and generates an output to at least a third rule module, and so forth, which may indicate to computing device 708 an in which such rule modules will be placed in decision tree. Building decision tree may include recursively performing mapping of execution results output by one tree and/or subtree to root nodes of another tree and/or subtree, for instance by using such execution results as execution parameters of a subtree. In this manner, computing device 708 may generate connections and/or combinations of one or more trees to one another to define overlaps and/or combinations into larger trees and/or combinations thereof. Such connections and/or combinations may be displayed by visual interface to user, for instance in first view, to enable viewing, editing, selection, and/or deletion by user; connections and/or combinations generated thereby may be highlighted, for instance using a different color, a label, and/or other form of emphasis aiding in identification by a user. In some embodiments, subtrees, previously constructed trees, and/or entire data structures may be represented and/or converted to rule modules, with graphical models representing them, and which may then be used in further iterations or steps of generation of decision tree and/or data structure. Alternatively or additionally subtrees, previously constructed trees, and/or entire data structures may be converted to APIs to interface with further iterations or steps of methods as described in this disclosure. As a further example, such subtrees, previously constructed trees, and/or entire data structures may become remote resources to which further iterations or steps of data structures and/or decision trees may transmit data and from which further iterations or steps of generation of data structure receive data, for instance as part of a decision in a given decision tree node.

Continuing to refer to FIG. 7, decision tree may incorporate one or more manually entered or otherwise provided decision criteria. Decision tree may incorporate one or more decision criteria using an application programmer interface (API). Decision tree may establish a link to a remote decision module, device, system, or the like. Decision tree may perform one or more database lookups and/or look-up table lookups. Decision tree may include at least a decision calculation module, which may be imported via an API, by incorporation of a program module in source code, executable, or other form, and/or linked to a given node by establishing a communication interface with one or more exterior processes, programs, systems, remote devices, or the like; for instance, where a user operating system has a previously existent calculation and/or decision engine configured to make a decision corresponding to a given node, for instance and without limitation using one or more elements of domain knowledge, by receiving an input and producing an output representing a decision, a node may be configured to provide data to the input and receive the output representing the decision, based upon which the node may perform its decision.

Now referring to FIG. 8A-F, an exemplary embodiment of a plurality of models used to generate each of representation of the plurality of representations. Processor 104 may take a plurality of ICD diagnoses codes, ICD procedure codes and medication prescriptions that have an association with at least 50 patients and are considered in the vocabulary. Since ICD-9 codes are different from ICD-10 codes, but the underlying text descriptions are similar, processor 104 may do a mapping from ICD-9 to ICD-10 to maintain the same phenotypic information. Finally, ICD-10 diagnoses codes may be shortened to three characters as keeping four or more characters provides little to no extra information for large scale pre-training. A vocabulary of size 28593 is constructed based on medication prescriptions, ICD-10 procedure codes and shortened ICD-10 diagnoses codes. To create the structured EHR sequence for structured EHR-BERT model pre-training processor 104 may randomly select one sequence of 512 consecutive medical codes from a given patient's timeline.

Figure 8A:
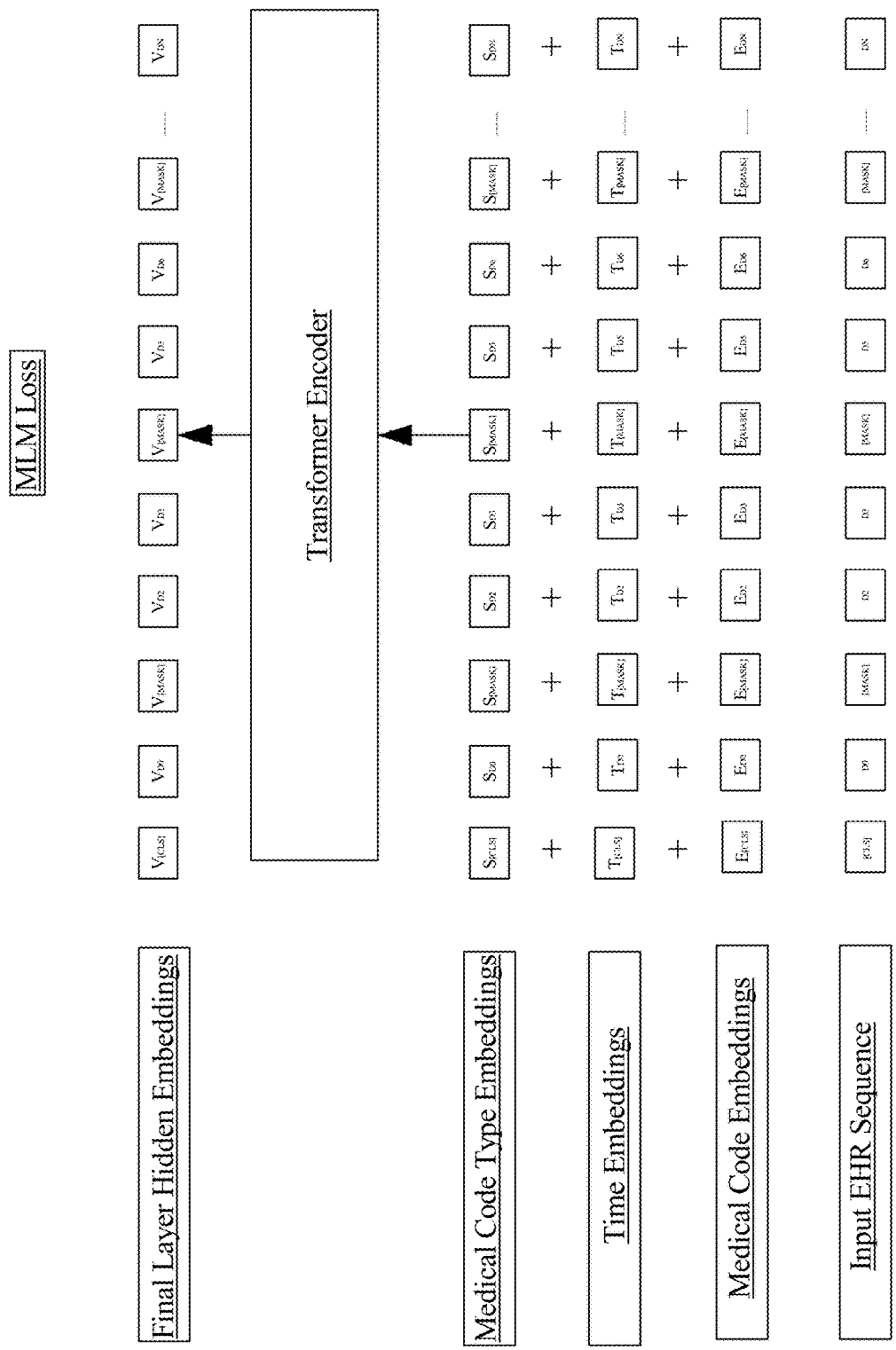
FIGS. 8A-F is an illustration of an exemplary an exemplary embodiment of a plurality of models used to generate each of representation of the plurality of representations.
Figure 8B:
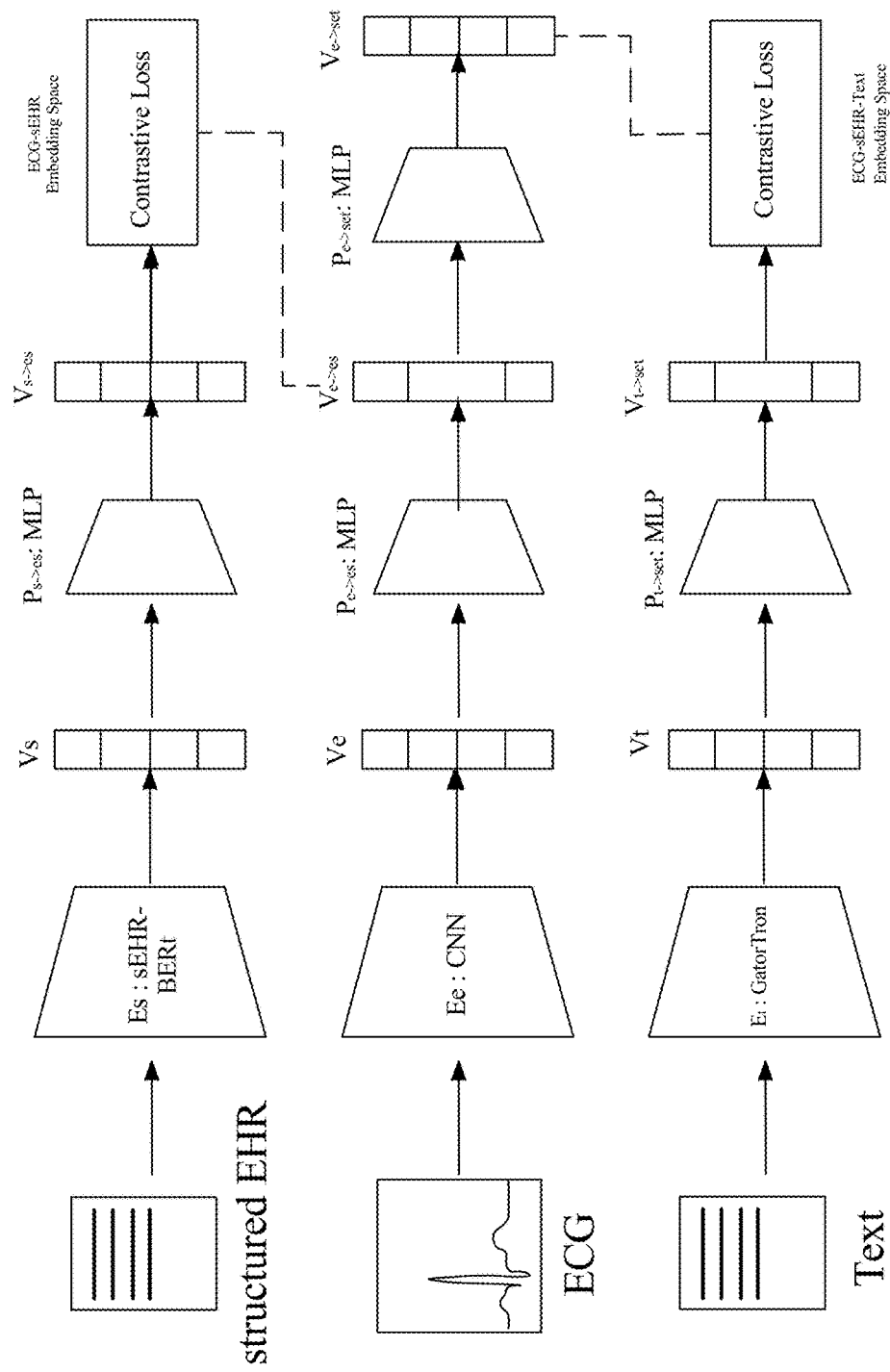

With continued reference to FIG. 8B, the first representations may be generated using MultiModal Versatile Networks (MMV), which apply contrastive learning to video, audio, text multi-modal data under the assumption that the video and audio modalities are more granular than the text modality. MMV assumes that applying contrastive loss in shared embedding space does not maintain the specificities of each domain, so two embedding spaces are learned i.e. a fine-grained space where video and audio are matched, and coarse-grained space where text is matched with video and audio domains.

With continued reference to FIG. 8B, in some cases, the first representations may not exhibit the same level of granularity as the third representation and the second representation. The first representations within a given time window surrounding the ECG signals 108 acquisition may have their timestamps rounded or trimmed based on the input length accepted by the corresponding encoders. This may be the cause of the different granularity of information between the third representation and the second representation. The MMV may be used to compare ECG signal 108 with structured EHR 120 in fine-grained joint third representation embedding space $\Omega_{es}$ and first representations in coarse-grained joint first representations $\Omega_{set}$.

With continued reference to FIG. 8B, A data set may include, $S = X_s \times X_e \times X_t$ consisting of triplets $\{(X_s^i, X_e^i, X_t^i)\}Mi=1$ where X Is the structured EHR sequence of the i-th sample, $X_e^i$ is the ECG waveform of the i-th sample, and $X_t^i$ is the text sequence of the i-th sample, M is the total number of samples in the training set. $X_s$, $X_e$, and $X_t$ denote the domain of the structured EHR, ECG and Text respectively.

With continued reference to FIG. 8B, In a non-limiting example, let $E_m : X_m \rightarrow R^{dm}$ be a parameterized model mapping from modality m to a modality specific embedding of dimension dm, where m can be s, e, t for structured EHR, ECG and Text respectively. Let $\Omega_s$ be a shared space between different modalities where modality specific representations are projected into to maximize or minimize the alignment between different modalities using the contrastive loss objective. To obtain the modality specific representations processor 104 may use a ResNet architecture customized to one dimension for the ECG encoder, the structured EHR-BERT encoder as described above for the structured EHR modality, and GatorTron encoder for the Text modality. The modality specific representations are projected into shared space using a two layered fully connected network. In another example, Let $P_{m \rightarrow s} : R^{dm} \rightarrow R^{ds}$ be a projection network mapping from representation of modality m to representation in shared space $\Omega_s$. Processor 104 may apply the contrastive loss between ECG and structured EHR in ECG-structured EHR joint embedding space, and contrastive loss between ECG and Text in structured EHR-ECG-Text joint embedding space so that granularity is maintained.

With continued reference to FIG. 8B, In another embodiment, Let $V_m^i$ may be the representation obtained by passing $X_m^i$ into modality specific encoder $E_m$, $V_{m-s}^i$ be the representation of $X_m$ in the shared space $\Omega_s$ obtained by passing $V_m^i$ into projection network $P_{m \rightarrow s}$, Then:

$$v_e^i = E_e(x_e^i)$$
$$v_s^i = E_s(x_s^i)$$
$$v_t^i = E_e(x_t^i)$$
$$v_{e-es}^i = P_{e \rightarrow es}(v_e^i)$$
$$v_{s-es}^i = P_{s \rightarrow es}(v_s^i)$$
$$v_{e-set}^i = P_{e \rightarrow set}(v_{e-es}^i)$$
$$v_{t-set}^i = P_{e \rightarrow es}(v_t^i)$$

Processor 104 may assume that all the above representations are $l_2$ normalized. Processor 104 may define the cosine similarity $s(x, y)$ between two $l_2$ normalized vectors, x, $y \in R^d$ as:

$$s(x,y) = x^T y$$

In a non-limiting example, in a given minibatch of size N, let $\tau \in R^+$ be the temperature parameter, $L_{es}$ be the contrastive loss between ECG and structured EHR, $L_i^{e \rightarrow s}$ be the contrastive loss directed from ECG to structured EHR, and $L_i^{s \rightarrow e}$ be the contrastive loss directed from structured EHR to ECG. Then, $$L_i^{e \rightarrow s} = -\log \frac{\exp(s(v_{e-es}^i, v_{s-es}^i)/T)}{\sum_{K=1}^N \exp(s(v_{e-es}^i, v_{s-es}^k)/T)}$$

$$L_i^{s \rightarrow e} = -\log \frac{\exp(s(v_{s-es}^i, v_{e-es}^i)/T)}{\sum_{K=1}^N \exp(s(v_{e-es}^i, v_{e-es}^k)/T)}$$

$$L_{es} = -\frac{1}{n} \sum_{i=1}^N (\lambda_{es} L_i^{e \rightarrow s} + (1 - \lambda_{es}) L_i^{s \rightarrow e})$$

Let $L_{et}$ be the contrastive loss between ECG and Text, $L_i^{e \rightarrow t}$ be the contrastive loss directed from ECG to Text, $L_i^{t \rightarrow e}$ be the contrastive loss directed from Text to ECG, then $$L_i^{e \rightarrow t} = -\log \frac{\exp(s(v_{e-set}^i, v_{t-set}^i)/T)}{\sum_{K=1}^N \exp(s(v_{e-set}^i, v_{t-set}^k)/T)}$$

$$L_i^{t \rightarrow e} = -\log \frac{\exp(s(v_{t-set}^i, v_{t-set}^i)/T)}{\sum_{K=1}^N \exp(s(v_{t-set}^i, v_{e-set}^k)/T)}$$

$$L_{es} = \frac{1}{n} \sum_{i=1}^N (\lambda_{es} L_i^{e \rightarrow t} + (1 - t) L_i^{t \rightarrow e})$$

the combination of which gives the overall loss:

$$L = L_{es} + L_{et}$$

where $\lambda es$ and $\lambda et$ are tunable hyperparameters $\in [0, 1]$

Figure 8C:
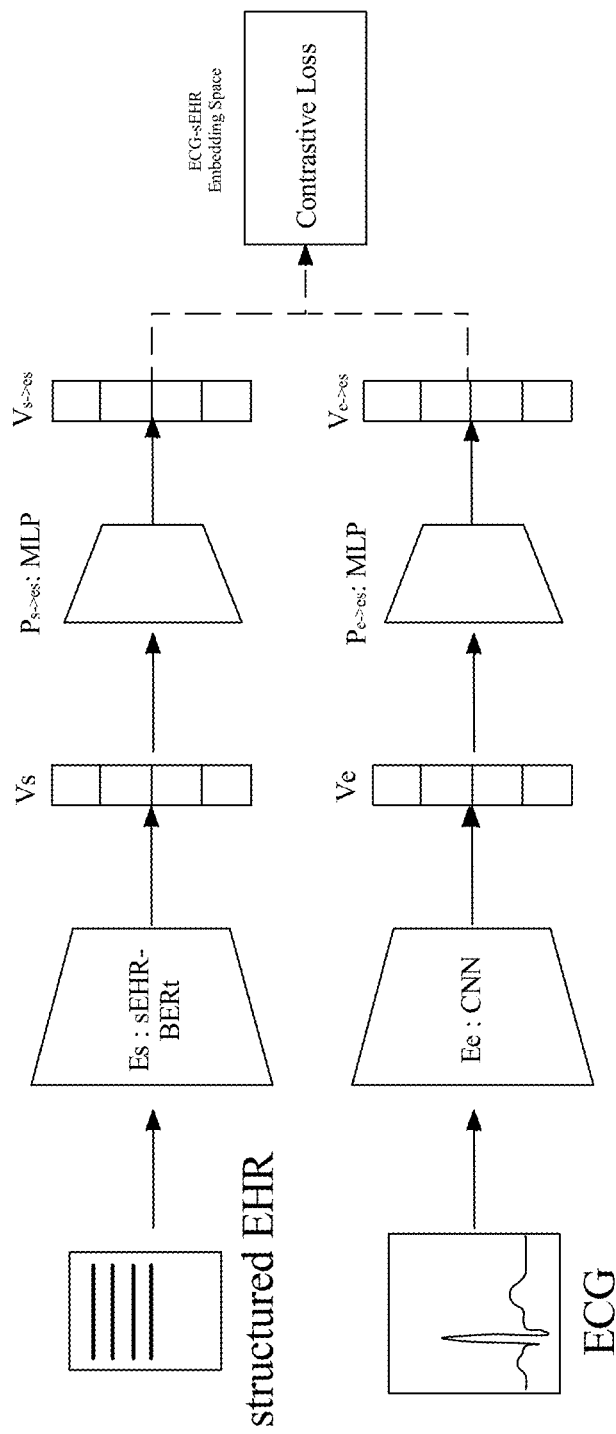

With continued reference to FIG. 8C, To create the $(X_e, X_s)$ ECG-structured EHR pairs, processor 104 may select an ECG of a given patient, $X_e$, and consider all the ICD diagnoses codes, ICD procedure codes and medication prescriptions associated with that patient within a period of one year prior, and one year subsequent, to the acquisition timestamp of that ECG. The medical codes restricted to this time range are arranged sequentially to form the initial structured EHR input sequence to the structured EHR-BERT model. Processor may use a maximum sequence length of 200 medical codes as input to the structured EHR-BERT encoder. The initial structured EHR input sequence with zeros if the structured EHR sequence length may be less than 200, and trimmed it by considering the nearest 200 medical codes to ECG acquisition timestamp if the structured EHR sequence length is greater than 200, to get the final $X_s$.

In the ECG-structured EHR model, processor 104 pairs ECGs with structured EHR data and apply multi-modal contrastive learning in joint ECG-structured EHR embedding space $\Omega_{es}$, discussed in greater detail herein above.

$$v_e^i = E_e(x_e^i)$$
$$v_s^i = E_s(x_s^i)$$
$$v_{e-es}^i = P_{e \rightarrow es}(v_e^i)$$
$$v_{s-es}^i = P_{s \rightarrow es}(v_s^i)$$

Let $L_{es}$ be the contrastive loss between ECG and structured EHR, $L_i^{e \rightarrow s}$ be the contrastive loss directed from ECG to structured EHR, and $L_i^{s \rightarrow e}$ be the contrastive loss directed from structured EHR to ECG. Then, the loss for the ECG-structured EHR model is given by:

$$L_{es} = \frac{1}{n} \sum_{i=1}^{N} (\lambda_{es} L_i^{e \to s} + (1-\lambda_{es}) L_i^{s \to e})$$

Contrastive loss between ECG and structured EHR is applied in ECG-sEHT joint embedding space where:

$$L_i^{e \to s} = -\log \frac{\exp(s(v_{e-es}^i, v_{s-es}^i)/T)}{\sum_{K=1}^{N} \exp(s(v_{e-es}^i, v_{s-es}^k)/T)}$$

$$L_i^{s \to e} = -\log \frac{\exp(s(v_{s-es}^i, v_{e-es}^i)/T)}{\sum_{K=1}^{N} \exp(s(v_{s-es}^i, v_{e-es}^k)/T)}$$

For a selected ECG, $X_e$, processor 104 may form multiple ECG-text pairs as an intermediate step. Textual data may include patient notes. Processor 104 may choose the one report that is closest in time to the ECG acquisition date, and pair it with the ECG, i.e. processor 104 forms pairs ($X_e$, $X_t^k$) with $X_t^k$ coming from different sources (k=ECG reports, ECHO reports, clinical documents, etc.). When forming the X, processor 104 may only use reports that were produced within 30 days after the ECG acquisition timestamp, except in the case of entity concatenation (described below) where processor 104 evaluated at reports produced in a time interval of one year pre- and post- the ECG acquisition timestamp.

From each of these intermediary reports, $X_t^k$, processor 104 may engage in an entity selection process An entity is a keyword that is medically relevant to the ECG being studied. By detecting those sentences in the notes that contain an entity, which may be chosen from a predetermined list, processor 104 can eliminate training on irrelevant data and improve the speed and potentially the performance of the representations produced.

Processor 104 may remove those sentences from the closest intermediary reports, $X_t^k$, that do not contain an entity. This is followed by randomly selecting one of these truncated intermediary reports to pair with the ECG. In the concatenation experiment, processor 104 may remove those sentences from the closest intermediary reports that do not contain an entity, but then concatenate all the truncated intermediary reports to form a final note, $X_t$, to pair with the ECG. In the entity concatenation experiment, processor 104 may focus not the sentences containing entities, but only the entities themselves, to form the final note, $X_t$. With the two latter experiments, the concatenation follows a priority order in which ECG reports precede ECHO reports, which in turn precede clinical, microbiology, pathology, radiology, and surgical notes.

Figure 8D:
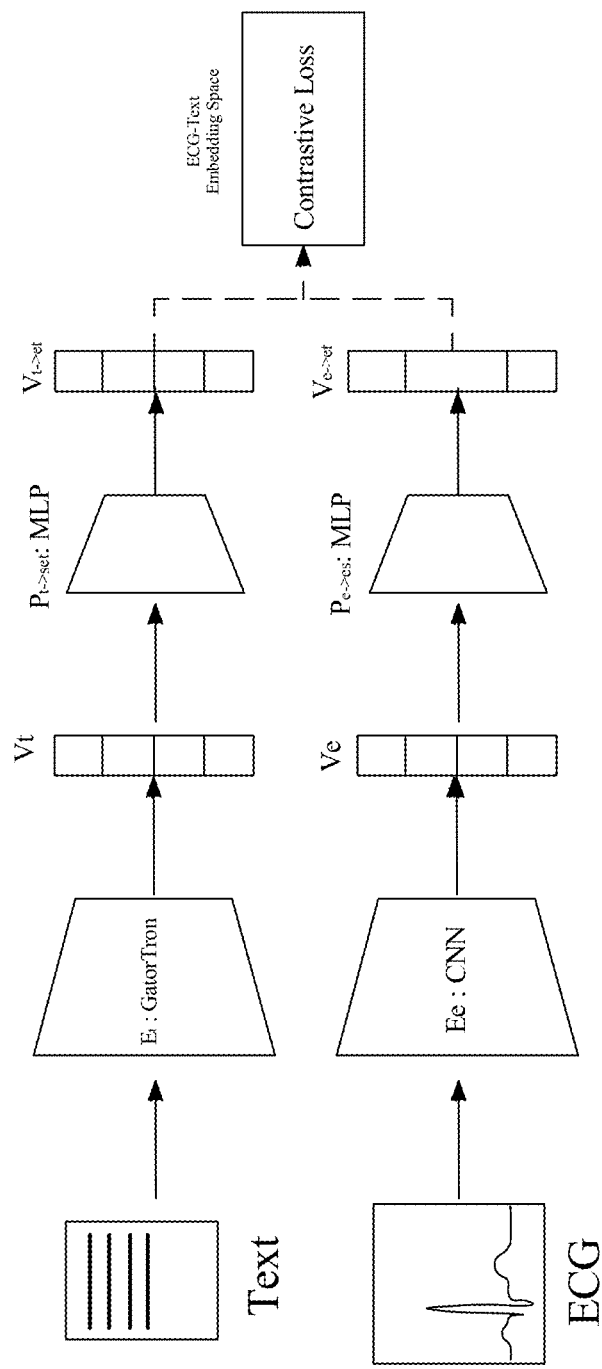

With continued reference to FIG. 8D, In the ECG-Text model, processor 104 may pair electrocardiogram signals with unstructured text data obtained from a variety of medical sources, including ECG reports, ECHO reports, pathology reports, radiology reports, microbiology reports and clinical documents. These are collectively referred to as patient notes in this work. Processor 104 may apply the contrastive learning between ECG and Text in joint ECG-Text Embedding space $\Omega_{et}$ $$v_e^i = E_e(x_e^i)$$

$$v_t^i = E_t(x_t^i)$$

$$v_{e-et}^i = P_{e \to et}(v_e^i)$$

$$v_{s-et}^i = P_{s \to et}(v_t^i)$$

In an embodiment, $L_{et}$ be the contrastive loss between ECG and Text, $L_i^{e \to t}$ be the contrastive loss directed from ECG to Text, and $L_i^{t \to e}$ be the contrastive loss directed from Text to ECG. Then, the loss for the ECG-Text model is given by:

$$L_{et} = \frac{1}{n} \sum_{i=1}^{N} (\lambda_{et} L_i^{e \to t} + (1-\lambda_{et}) L_i^{t \to e})$$

$$L_i^{s \to t} = -\log \frac{\exp(s(v_{e-et}^i, v_{t-et}^i)/T)}{\sum_{K=1}^{N} \exp(s(v_{e-et}^i, v_{t-et}^k)/T)}$$

Counts for ECGs and unique patients for each downstream task cohort.

$$L_i^{t \to e} = -\log \frac{\exp(s(v_{t-et}^i, v_{e-et}^i)/T)}{\sum_{K=1}^{N} \exp(s(v_{t-et}^i, v_{e-et}^k)/T)}$$

With continued reference to FIGS. 8A-D, the ECGs representations learnt using a plurality of models may be evaluated on various downstream tasks. Processor 104 may use the representations obtained using the three models presented in this disclosure as inputs to a logistic regression architecture to train various linear models for disease classification tasks. These diseases may include Atherosclerotic cardiovascular disease (ASCVD), Myocarditis, Pulmonary Hypertension (PH), Left ventricular ejection fraction (LVEF), Atrial fibrillation in Normal Sinus Rhythm (AFib in NSR). Processor 104 may compare the performance of the linear classification models against two baseline supervised learning models; the first may be a neural net trained from scratch using random initialization of its weights, while the second may be a large-scale multitask learning ('MTL') model, described below. Processor 104 may evaluate the performance (AUC) of various models on linear classification task trained across different disease cohorts and across different fractions of the training set, i.e. 1%, 10%, 100%.

With continued reference to FIGS. 8A-D, all models, across diseases, show improvement over the models trained from scratch with random initialization. The ECG-structured EHR model may be the overall best-performing model with a slight drop from large scale ECG-MTL model in case of LVEF and PH diseases. The difference between the ECG-structured EHR and ECG-Text models varies between 1-2%.

With continued reference to FIGS. 8A-D, In high data environments such as PH, LVEF and AFib in NSR, the drop in performance between a model trained on the full training data (100%) and of 10% of the training data may not be too large. The large drop in performance on the 1% subset in diseases such as Myocarditis can be explained by the small cohort size of even the full training set.

With continued reference to FIGS. 8A-D, Using ECG representations obtained from ECG-structured EHR, processor 104 observes that linear classification models trained on 10% of training data across all diseases achieve performance comparable to or better than that of the random weight initialization model trained on the full training dataset, showing the effectiveness of the learned representations for label efficiency.

With continued reference to FIGS. 8A-D, Processor 104 may observe that the representations learned via self-supervised learning techniques help to better distinguish datum that comes from out of the distribution under consideration. Processor 104 may demonstrate this using representations obtained from our EHR model to distinguish between two disparate ECG datasets. Processor 104 may take the proprietary ECG pulmonary hypertension (PH) cohort as the 'In Distribution', and holter ECGS from the open-source St Petersburg INCART 12-lead Arrhythmia Database as the 'Out Distribution'. Processor 104 may trains a CNN network (PH model) in supervised setting on our PH training data to compare the performance of both the representations. Processor 104 may use three metrics to determine whether the data is in or out of distribution—the Relative Mahalanobis Distance (RMD), the Class Conditional Mahalanobis Distance (CCMD), and the Cleanlab Out of distribution. While Relative Mahalanobis Distance is based on mahalanobis distance of embeddings from nearest predicted class, clean lab uses a K-Nearest Neighbor based approach to distinguish In vs Out distribution samples. We use the representations from the EHR model and the PH model, and show that that the rejection rate at different significance levels is much higher when the EHR model representations are used. The results may show that generic ECG representations are better at detecting out-of-distribution data than model specific representations.

With continued reference to FIGS. 8A-D, processor 104 may be configured to identify a quality of a plurality of representations 124. A plurality of representations 124 is said to be good if it satisfies several criteria. The criteria may include expressiveness, abstraction and invariance, and disentanglement. Expressiveness may include the ability of the plurality of representations 124 to represent a large number of input configurations. Abstraction and invariance may include the ability of the plurality of representations 124 to encode high level information, and thus be invariant to small local variations of the data. Disentanglement may include the ability to learn all explanatory features while preserving orthogonality of distinct factors. The quality of a plurality of representations 124 may be quantified by the improvement in performance it leads to in a downstream task, although there is often a trade-off between good performance over a wide range of tasks and excellent performance in a specialized task. If the representations are learned via a proxy task, such as similarity in contrastive learning, performance on the proxy task can serve as a metric for measuring quality of the representation.

Figure 8E:
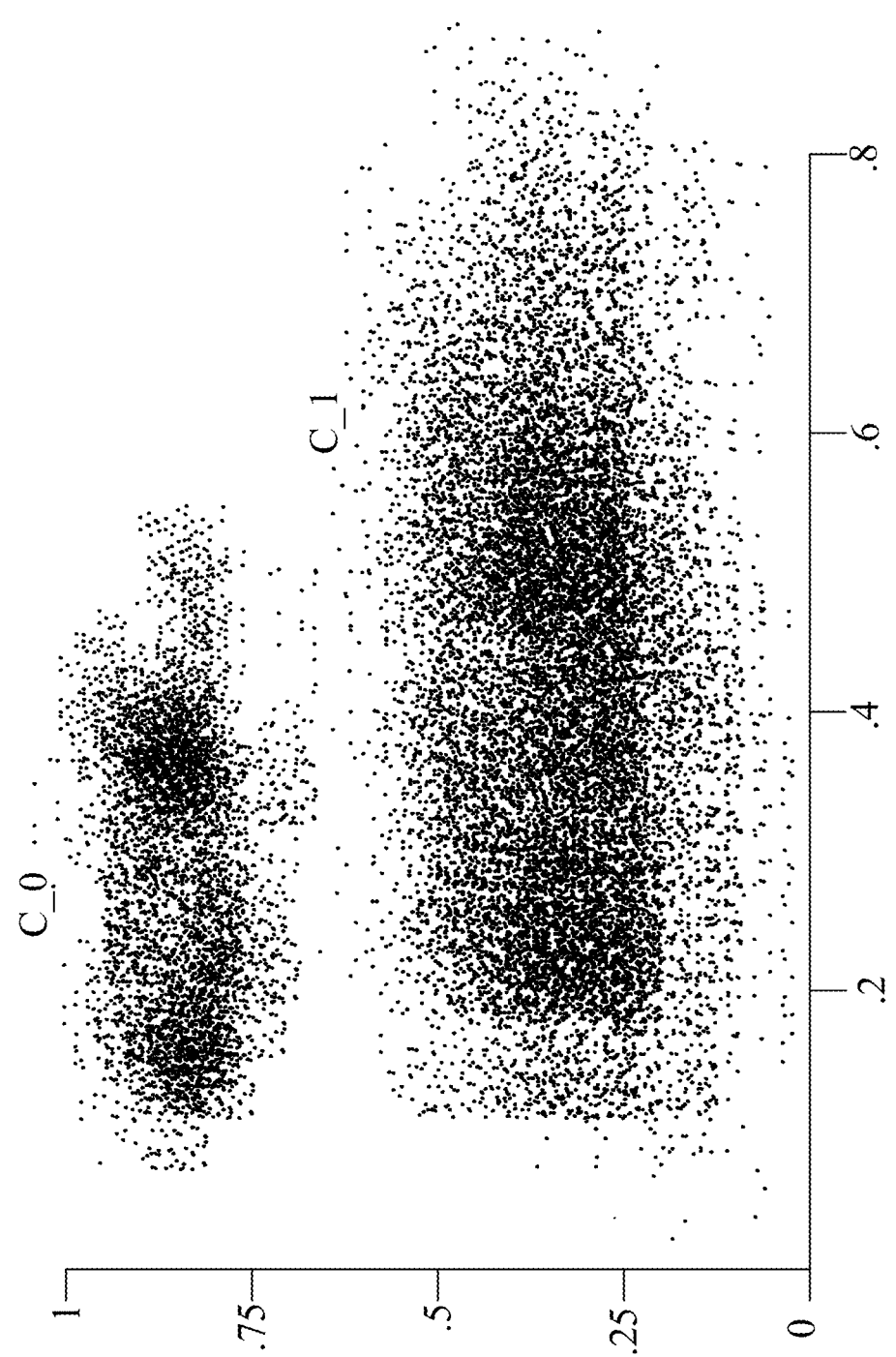
Figure 8F:
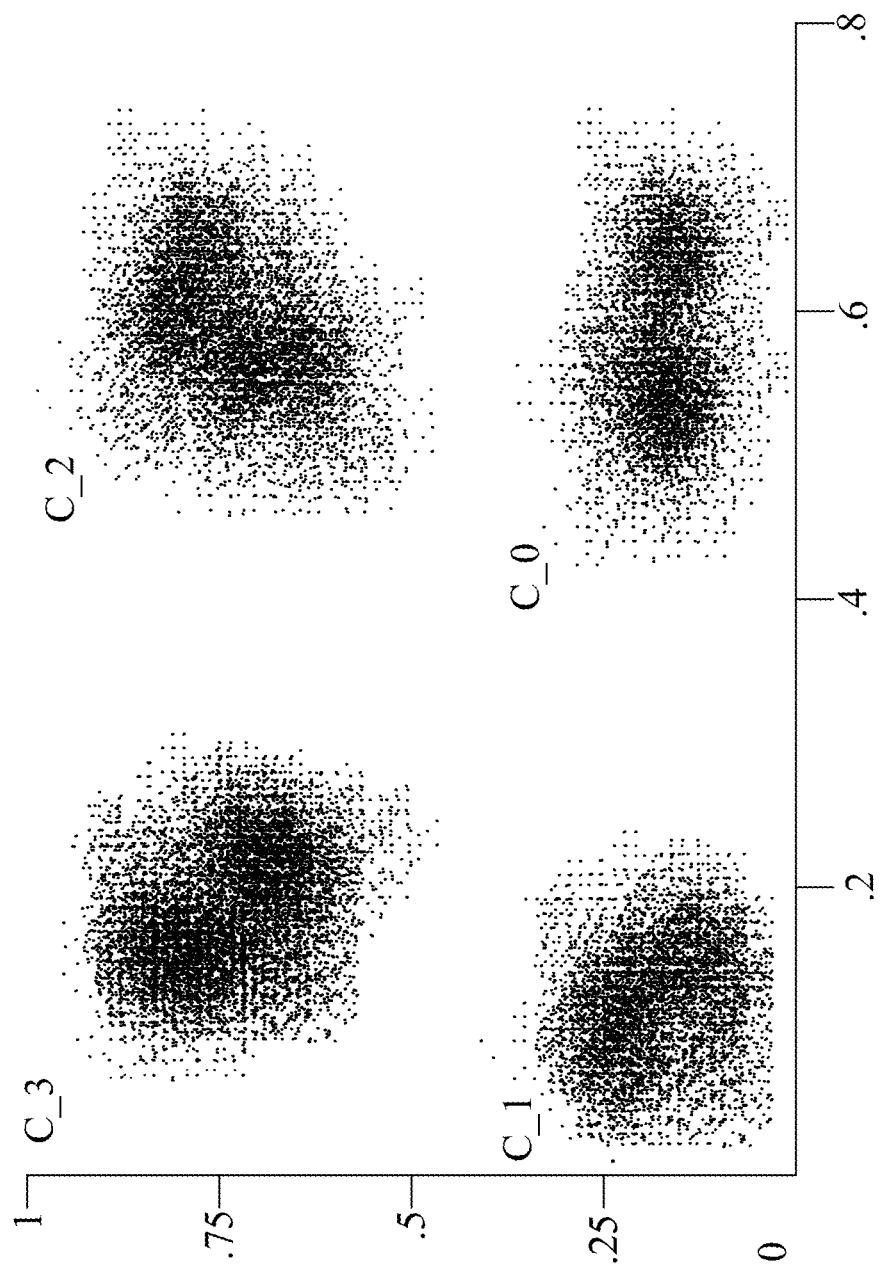

With continued reference to FIGS. 8E-F, Representations can be used to better and more quickly cluster similar data samples together. We demonstrate this by comparing the clustering on the PH cohort obtained using the EHR model and the PCLR model representations. Processor 104 may a density based clustering algorithms, HDBSCAN, performed on the UMAP space of positive ECGs. The cluster strength for a cluster i, $C_i$ is given by:

$$C_i = \frac{P_i \log(P_i + N_i)}{P_i + N_i}$$

where Pi is the count of positive ECGs in the ith cluster, and Ni is the count of negative ECGs in the ith cluster. The cluster strength value above quantifies the proportion of positives along with total count of ECGs in a particular cluster. To compare the clustering ability of two sets of embeddings, we use the overall cluster strength:

$$EC = \frac{\sum_i C_i}{\sum_j \log(P_j + N_j)}$$

FIGS. 8E-F show the results of clustering on the EHR model and PCLR model embeddings, respectively. The former has an overall cluster strength of 0.5149, while the PCLR embeddings cluster with an overall strength of 0.3125.

Figure 9:
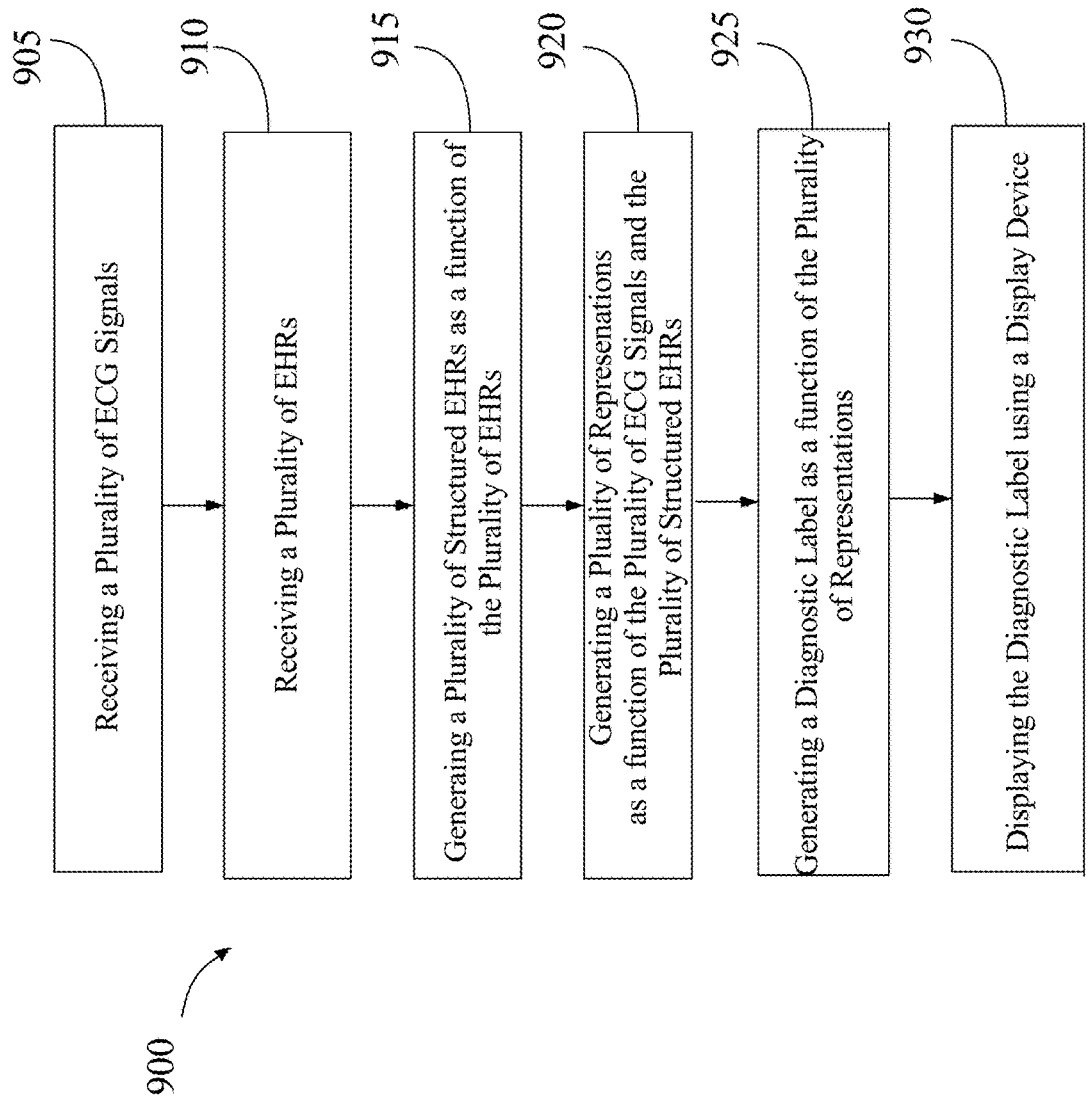
FIG. 9 is a flow diagram of an exemplary method for generating a diagnostic label.

Referring now to FIG. 9, a flow diagram of an exemplary method 800 for generating a diagnostic label is illustrated. At step 905, method 900 includes receiving, using at least a processor, a plurality of electrocardiogram signals from a user. This may be implemented as described and with reference to FIGS. 1-8.

Still referring to FIG. 9, At step 910, method 900 includes receiving, using the at least a processor, a plurality of electronic health records from the user, wherein the plurality of electronic health records includes a plurality of metadata. This may be implemented as described and with reference to FIGS. 1-8. In an embodiment, the plurality of metadata includes a plurality of textual data. In another embodiment, the plurality of electronic medical records include a plurality of health data.

Still referring to FIG. 9 At step 915, method 900 includes generating, using the at least a processor, a plurality of structured electronic health records using the plurality of electronic health records. This may be implemented as described and with reference to FIGS. 1-8. In an embodiment, generating the plurality of structured electronic health records may include classifying the plurality of health data to a plurality of diagnostic codes. In another embodiment, generating the plurality of structured electronic health records comprises generating the plurality of structured electronic health records using a structure classifier.

Still referring to FIG. 9 At step 920, method 900 includes generating, using the at least a processor, a plurality of representations as a function of the plurality of electrocardiogram signals and the plurality of structured electronic health records using a representation machine learning model. This may be implemented as described and with reference to FIGS. 1-8. In an embodiment, the plurality of representations may include a first representation, a second representation, or third representation.

Still referring to FIG. 9 At step 925, method 900 includes generating, using the at least a processor, a diagnostic label as a function of the plurality of representations. This may be implemented as described and with reference to FIGS. 1-8. The method may additionally include generating, using the at least a processor, a diagnostic report as a function of the diagnostic label. In some embodiment, the method may be configured to generate, using the at least a processor, a plurality of graphical data as a function of the plurality of representations; and identify, using the at least a processor, one or more representation clusters as a function of the plurality of graphical data.

Still referring to FIG. 9 At step 920, method 900 includes displaying, using the at least a processor, the diagnostic label using a display device. This may be implemented as described and with reference to FIGS. 1-8.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 10:
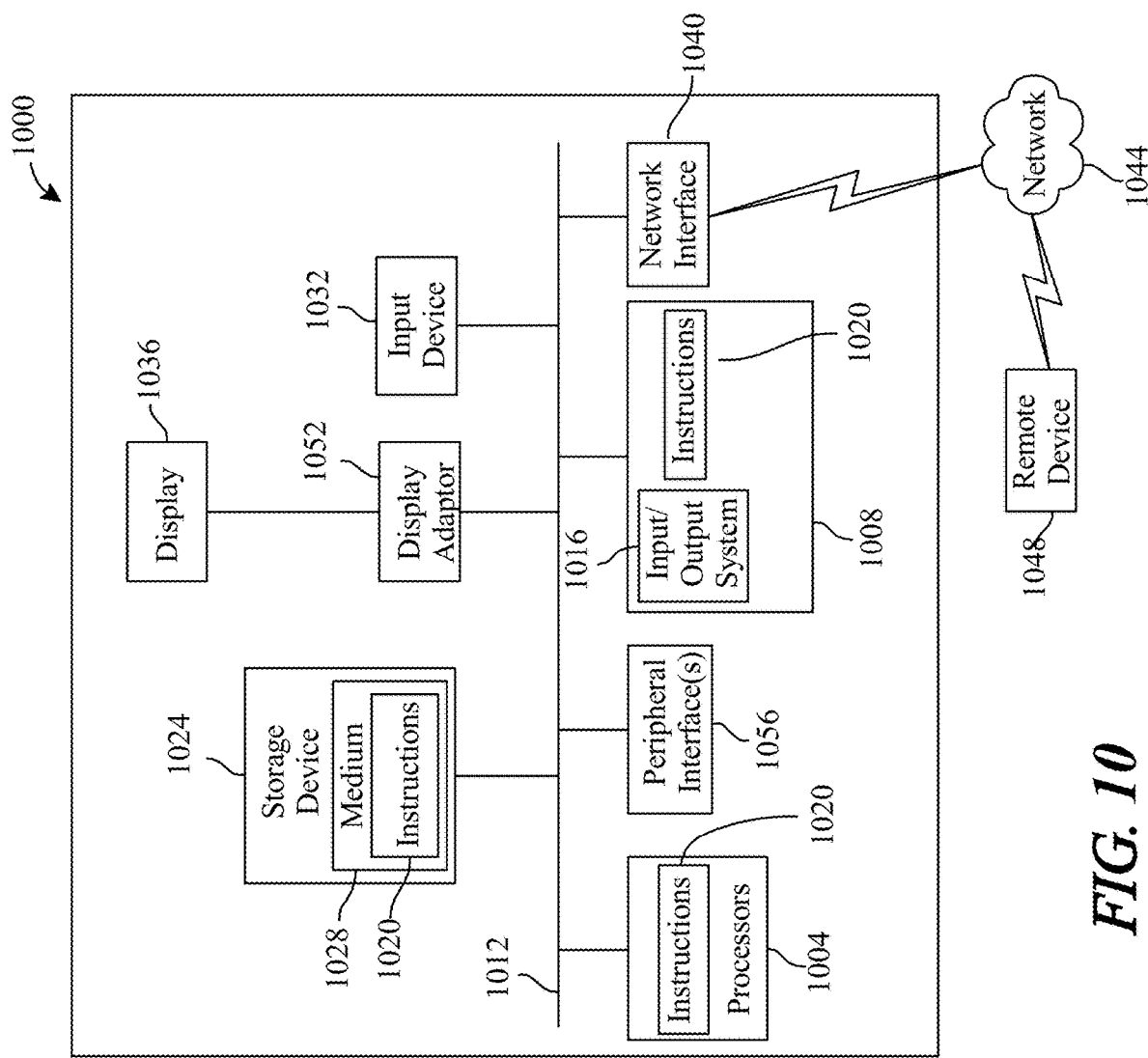
FIG. 10 is a block diagram of a computing system that can be used to implement any one or more of the methodologies disclosed herein and any one or more portions thereof.

FIG. 10 shows a diagrammatic representation of one embodiment of a computing device in the exemplary form of a computer system 1000 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 1000 includes a processor 1004 and a memory 1008 that communicate with each other, and with other components, via a bus 1012. Bus 1012 may include any of several types of bus structures including, but not limited to, a memory bus, a memory controller, a peripheral bus, a local bus, and any combinations thereof, using any of a variety of bus architectures.

Processor 1004 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 1004 may be organized according to Von Neumann and/or Harvard architecture as a non-limiting example. Processor 1004 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC).

Memory 1008 may include various components (e.g., machine-readable media) including, but not limited to, a random-access memory component, a read only component, and any combinations thereof. In one example, a basic input/output system 1016 (BIOS), including basic routines that help to transfer information between elements within computer system 1000, such as during start-up, may be stored in memory 1008. Memory 1008 may also include (e.g., stored on one or more machine-readable media) instructions (e.g., software) 1020 embodying any one or more of the aspects and/or methodologies of the present disclosure. In another example, memory 1008 may further include any number of program modules including, but not limited to, an operating system, one or more application programs, other program modules, program data, and any combinations thereof.

Computer system 1000 may also include a storage device 1024. Examples of a storage device (e.g., storage device 1024) include, but are not limited to, a hard disk drive, a magnetic disk drive, an optical disc drive in combination with an optical medium, a solid-state memory device, and any combinations thereof. Storage device 1024 may be connected to bus 1012 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 1024 (or one or more components thereof) may be removably interfaced with computer system 1000 (e.g., via an external port connector (not shown)). Particularly, storage device 1024 and an associated machine-readable medium 1028 may provide nonvolatile and/or volatile storage of machine-readable instructions, data structures, program modules, and/or other data for computer system 1000. In one example, software 1020 may reside, completely or partially, within machine-readable medium 1028. In another example, software 1020 may reside, completely or partially, within processor 1004.

Computer system 1000 may also include an input device 1032. In one example, a user of computer system 1000 may enter commands and/or other information into computer system 1000 via input device 1032. Examples of an input device 1032 include, but are not limited to, an alphanumeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 1032 may be interfaced to bus 1012 via any of a variety of interfaces (not shown) including, but not limited to, a serial interface, a parallel interface, a game port, a USB interface, a FIRE-WIRE interface, a direct interface to bus 1012, and any combinations thereof. Input device 1032 may include a touch screen interface that may be a part of or separate from display 1036, discussed further below. Input device 1032 may be utilized as a user selection device for selecting one or more graphical representations in a graphical interface as described above.

A user may also input commands and/or other information to computer system 1000 via storage device 1024 (e.g., a removable disk drive, a flash drive, etc.) and/or network interface device 1040. A network interface device, such as network interface device 1040, may be utilized for connecting computer system 1000 to one or more of a variety of networks, such as network 1044, and one or more remote devices 1048 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus, or other relatively small geographic space), a telephone network, a data network associated with a telephone/voice provider (e.g., a mobile communications provider data and/or voice network), a direct connection between two computing devices, and any combinations thereof. A network, such as network 1044, may employ a wired and/or a wireless mode of communication. In general, any network topology may be used. Information (e.g., data, software 1020, etc.) may be communicated to and/or from computer system 1000 via network interface device 1040.

Computer system 1000 may further include a video display adapter 1052 for communicating a displayable image to a display device, such as display device 1036. Examples of a display device include, but are not limited to, a liquid crystal display (LCD), a cathode ray tube (CRT), a plasma display, a light emitting diode (LED) display, and any combinations thereof. Display adapter 1052 and display device 1036 may be utilized in combination with processor 1004 to provide graphical representations of aspects of the present disclosure. In addition to a display device, computer system 1000 may include one or more other peripheral output devices including, but not limited to, an audio speaker, a printer, and any combinations thereof. Such peripheral output devices may be connected to bus 1012 via a peripheral interface 1056. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. An apparatus for generating a diagnostic label, wherein the apparatus comprises:
   at least a processor; and
   a memory communicatively connected to the at least a processor, wherein the memory contains instructions configuring the at least a processor to:
      receive a plurality of electrocardiogram signals from a user;
      receive a plurality of electronic health records from the user, wherein the plurality of electronic health records includes a plurality of metadata, wherein receiving the plurality of electronic health records further comprises:
         utilizing optical character recognition (OCR) to convert the plurality of electronic health records into machine-encoded text; and
         extracting features from the plurality of electronic health records to reduce a dimensionality of a representation of the plurality of health records;
      generate a plurality of structured electronic health records using the plurality of electronic health records, wherein the plurality of structured electronic health records includes a plurality of diagnostic codes, wherein generating the plurality of structured electronic health records further comprises:
         classifying health data in the plurality of diagnostic codes comprising at least a corresponding time code representing a medical condition of the user within a given time period;
      generate a plurality of representations as a function of the plurality of electrocardiogram signals and the plurality of structured electronic health records using a representation machine learning model, wherein generating the plurality of representations comprises:
         generating representation training data, wherein generating the representation training data comprises:
            inputting electrocardiogram signal representations with dummy pixels into the representation machine learning model; and
            outputting the representation training data comprising the electrocardiogram signal representations with the dummy pixels replaced with filled-in values;
         training the representation machine learning model using representation training data; and
         generating the plurality of representations as a function of the plurality of electrocardiogram signals and the plurality of structured electronic health records using the trained representation machine learning model;
      generate a diagnostic label as a function of the plurality of representations; and
      display the diagnostic label using a display device.

2. The apparatus of claim 1, wherein the plurality of representations comprises a first representation.

3. The apparatus of claim 1, wherein the plurality of representations comprises a second representation.

4. The apparatus of claim 1, wherein the plurality of representations comprises a third representation.

5. The apparatus of claim 1, wherein the plurality of metadata comprises a plurality of textual data.

6. The apparatus of claim 1, wherein generating the plurality of structured electronic health records comprises generating the plurality of structured electronic health records using a structure classifier.

7. The apparatus of claim 1, wherein the memory further instructs the at least a processor to:
    generate a plurality of graphical data as a function of the plurality of representations; and
    identify one or more representation clusters as a function of the plurality of graphical data.

8. The apparatus of claim 1, wherein the memory further instructs the at least a processor to generate a diagnostic report as a function of the diagnostic label.

9. A method for generating a diagnostic label, wherein the method comprises:
    receiving, using at least a processor, a plurality of electrocardiogram signals from a user;
    receiving, using the at least a processor, a plurality of electronic health records from the user, wherein the plurality of electronic health records includes a plurality of metadata, wherein receiving the plurality of electronic health records further comprises:
        utilizing optical character recognition (OCR) to convert the plurality of electronic health records into machine-encoded text; and
        extracting features from the plurality of electronic health records to reduce a dimensionality of a representation of the plurality of health records;
    generating, using the at least a processor, a plurality of structured electronic health records using the plurality of electronic health records, wherein the plurality of structured electronic health records includes a plurality of diagnostic codes, wherein generating the plurality of structured electronic health records further comprises:
        classifying health data in the plurality of diagnostic codes comprising at least a corresponding time code representing a medical condition of the user within a given time period;
    generating, using the at least a processor, a plurality of representations as a function of the plurality of electrocardiogram signals and the plurality of structured electronic health records using a representation machine learning model, wherein generating the plurality of representations comprises:
        generating representation training data, wherein generating the representation training data comprises:
            inputting electrocardiogram signal representations with dummy pixels into the representation machine learning model; and
            outputting the representation training data comprising the electrocardiogram signal representations with the dummy pixels replaced with filled-in values;
        training the representation machine learning model using representation training data; and
        generating the plurality of representations as a function of the plurality of electrocardiogram signals and the plurality of structured electronic health records using the trained representation machine learning model;
    generating, using the at least a processor, a diagnostic label as a function of the plurality of representations; and
    displaying, using the at least a processor, the diagnostic label using a display device.

10. The method of claim 9, wherein the plurality of representations comprises a first representation.

11. The method of claim 9, wherein the plurality of representations comprises a second representation.

12. The method of claim 9, wherein the plurality of representations comprises a third representation.

13. The method of claim 9, wherein the plurality of metadata comprises a plurality of textual data.

14. The method of claim 9, wherein the method further comprises generating, using the at least a processor, the plurality of structured electronic health records using a structure classifier.

15. The method of claim 9, wherein the method further comprises:
    generating, using the at least a processor, a plurality of graphical data as a function of the plurality of representations; and
    identifying, using the at least a processor, one or more representation clusters as a function of the plurality of graphical data.

16. The method of claim 9, wherein the method further comprises generating, using the at least a processor, a diagnostic report as a function of the diagnostic label.

* * * * *